United States Patent
Gaster et al.

[11] Patent Number: 5,990,133
[45] Date of Patent: Nov. 23, 1999

[54] INDOLE DERIVATIVES AS 5-HT RECEPTOR ANTAGONIST

[75] Inventors: Laramie Mary Gaster, Bishop's Stortford; Paul Adrian Wyman, Epping; Keith Raymond Mulholland, Harlow; David Thomas Davies, Ware; David Malcolm Duckworth, Bishop's; Ian Thomson Forbes, Stevenage; Graham Elgin Jones, Hertford, all of United Kingdom

[73] Assignee: SmithKline Beecham p.l.c., Brentford, United Kingdom

[21] Appl. No.: 08/875,506

[22] PCT Filed: Jan. 26, 1996

[86] PCT No.: PCT/EP96/00368

§ 371 Date: Oct. 16, 1997

§ 102(e) Date: Oct. 16, 1997

[87] PCT Pub. No.: WO96/23783

PCT Pub. Date: Aug. 8, 1996

[30] Foreign Application Priority Data

| Feb. 2, 1995 | [GB] | United Kingdom | 9502052 |
| Apr. 25, 1995 | [GB] | United Kingdom | 9508327 |
| May 3, 1995 | [GB] | United Kingdom | 9508967 |
| Aug. 17, 1995 | [GB] | United Kingdom | 9516845 |
| Aug. 26, 1995 | [GB] | United Kingdom | 9517542 |
| Sep. 12, 1995 | [GB] | United Kingdom | 9518574 |

[51] Int. Cl.[6] .................. A61K 31/44; C07D 401/10; C07D 403/10
[52] U.S. Cl. ........................... 514/337; 546/277.1
[58] Field of Search ........................... 546/277.1; 514/337

[56] References Cited

FOREIGN PATENT DOCUMENTS

| WO 92/05170 | 4/1992 | WIPO. |
| WO 94/04533 | 3/1994 | WIPO. |
| WO 94/22871 | 10/1994 | WIPO. |

Primary Examiner—Alan L. Rotman
Attorney, Agent, or Firm—Linda E. Hall; Stephen A. Venetianer; Charles M. Kinzig

[57] ABSTRACT

A compound of formula (I) or a salt thereof:

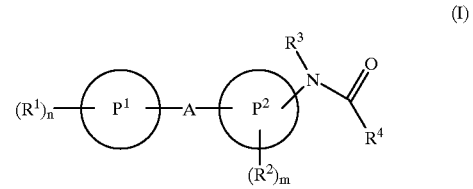

wherein:

$P^1$ is pyridyl;

$P^2$ is phenyl;

A is a bond or a chain of 1 to 5 atoms optionally substituted by $C_{1-6}$alkyl;

$R^1$ and $R^2$ groups are each independently hydrogen, $C_{1-6}$alkyl optionally substituted by $NR^{12}R^{13}$, $C_{2-6}$alkenyl, $C_{2-6}$alkynyl, cyano, halogen, $CF_3$, $NR^{12}R^{13}$, CHO, $OCF_3$, $COR^{14}$, $CH_2OR^{14}$ or $OR^{14}$ where $R^{12}$, $R^{13}$ and $R^{14}$ are independently hydrogen or $C_{1-6}$alkyl;

n and m are independently 0, 1 or 2;

$R^3$ is hydrogen or $C_{1-6}$ alkyl;

$R^4$ is a group of formula (i):

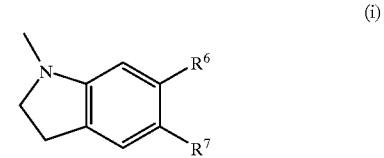

in which:

$R^6$ and $R^7$ are independently hydrogen, $C_{1-6}$ alkyl optionally substituted by one or more fluorine atoms, $C_{1-6}$alkylthio, $C_{1-6}$alkoxy or halogen.

14 Claims, No Drawings

INDOLE DERIVATIVES AS 5-HT RECEPTOR ANTAGONIST

This invention relates to compounds having pharmacological activity, processes for their preparation, to compositions containing them and to their use in the treatment of CNS disorders.

WO 94/04533 (SmithKline Beecham plc) describes indole and indoline derivatives which are described as possessing $5HT_{2C}$ receptor antagonist activity. A structurally distinct class of compounds has now been discovered, which have been found to have $5HT_{2C}$ receptor antagonist activity. Certain compounds of the invention also exhibit $5HT_{2B}$ antagonist activity. $5HT_{2C/2B}$ receptor antagonists are believed to be of potential use in the treatment of CNS disorders such as anxiety, depression, epilepsy, obsessive compulsive disorders, migraine, Alzheimers disease, sleep disorders, feeding disorders such as anorexia and bulimia, panic attacks, withdrawal from drug abuse such as cocaine, ethanol, nicotine and benzodiazepines, schizophrenia, and also disorders associated with spinal trauma and/or head injury such as hydrocephalus. Compounds of the invention are also expected to be of use in the treatment of certain GI disorders such as IBS as well as microvascular diseases such as macular oedema and retinopathy.

The present invention therefore provides, in a first aspect, a compound of formula (I) or a salt thereof:

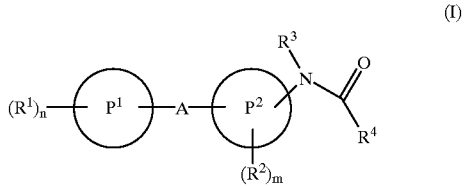

(I)

wherein:

$p^1$ and $p^2$ are independently phenyl, aromatic or partially saturated monocyclic or bicyclic heterocyclic rings containing up to three heteroatoms selected from nitrogen, oxygen or sulphur, A is a bond, a chain of 1 to 5 atoms optionally substituted by $C_{1-6}$ alkyl or A is an optionally substituted phenyl or an optionally substituted 5- to 7-membered heterocyclic ring containing up to three heteroatoms selected from nitrogen, oxygen or sulphur;

$R^1$ and $R^2$ groups are each independently hydrogen, $C_{1-6}$ alkyl optionally substituted by $NR^{12}R^{13}$, $C_{2-6}$ alkenyl, $C_{2-6}$ alkynyl, $C_{1-6}$ alkylthio, cyano, nitro, halogen, $CF_3$, $C_2F_5$, $NR^{12}R^{13}$, $CONR^{12}R^{13}$, $NR^{12}COR^{13}$, $S(O)_p$ $NR^{12}R^{13}$, CHO, $OCF_3$, $SCF_3$, $COR^{14}$, $CH_2OR^{14}$, $CO_2R^{14}$ or $OR^{14}$ where p is 1 or 2 and $R^{12}$, $R^{13}$ and $R^{14}$ are independently hydrogen, $C_{1-6}$ alkyl, optionally substituted aryl or optionally substituted aryl$C_{1-6}$alkyl;

n and m are independently 0, 1 or 2;

$R^3$ is hydrogen or $C_{1-6}$ alkyl;

$R^4$ is a group of formula (i):

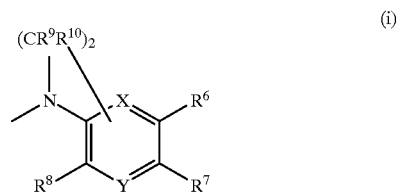

(i)

in which:

X and Y are both nitrogen, one is nitrogen and the other is carbon or a $CR^5$ group or one is a $CR^5$ group and the other is carbon or a $CR^5$ group;

$R^5$, $R^6$, $R^7$ and $R^8$ groups are independently hydrogen, $C_{1-6}$ alkyl optionally substituted by one or more fluorine atoms, $C_{2-6}$ alkenyl, $C_{3-6}$ cycloalkyl, $C_{3-6}$ cycloalkyl$C_{1-6}$alkoxy, $C_{2-6}$ alkynyl, $C_{3-6}$ cycloalkyloxy, $C_{3-6}$ cycloalkyl-$C_{1-6}$ alkyl, $C_{1-6}$ alkylthio, $C_{3-6}$ cycloalkylthio, $C_{3-6}$ cycloalkyl-$C_{1-6}$ alkylthio, $C_{1-6}$alkoxy, hydroxy, halogen, nitro, $OCF_3$, $SCF_3$, $SO_2CF_3$, $SO_2F$, formyl, $C_{2-6}$ alkanoyl, cyano, optionally substituted phenyl or thienyl, $NR^{12}R^{13}$, $CONR^{12}R^{13}$ or $CO_2R^{14}$ where where $R^{12}$, $R^{13}$ and $R^{14}$ are as defined for $R^1$; or $R^6$ and $R^7$ form part of an optionally substituted 5- or 6-membered carbocyclic or heterocyclic ring;

$R^9$ and $R^{10}$ are independently hydrogen or $C_{1-6}$ alkyl;

$C_{1-6}$ Alkyl groups, whether alone or as part of another group, may be straight chain or branched Suitably A is a bond or a chain of 1 to 5 atoms optionally substituted by $C_{1-6}$ alkyl. Examples of such chains include $(CH_2)_pX$ or $X(CH_2)_p$ where p is 1 to 4 and X is CO, O, S(O)$_x$ where x is 0 to 2 or A is NR, CONR, NRCO, NRCONR, CO, CH(OH), $C_{1-6}$alkyl, CH=CH, CH=CF, CF=CF, O, S(O)$_x$ where x is 1 or 2, NR, or $NRSO_2$ where R is hydrogen or $C_{1-6}$ alkyl. Preferably A is a bond or a group $CH_2O$, $OCH_2$, or O.

Suitably A is an optionally substituted phenyl group or an optionally substituted 5- or 6-membered heterocyclic ring containing up to three heteroatoms selected from nitrogen, oxygen or sulphur. Preferably A is thiazolyl, isothiazolyl, oxazolyl, isoxazolyl, thiadiazolyl, triazolyl, pyridyl, pyrimidyl or pyrazinyl. Most preferably A is thiazolyl. Optional substituents when A is a phenyl or a heterocyclic group include those groups $R^1$ and $R^2$ listed above The urea moiety can be attached to a carbon or any available nitrogen atom of the ring $P^2$, preferably it is attached to a carbon atom. Suitable moieties when the rings $P^1$ and $p^2$ are 5-membered aromatic heterocyclic rings include isothiazolyl, isoxazolyl, thiadiazolyl, oxadiazolyl and triazolyl. Suitable moieties when the rings $p^1$ and $p^2$ are 6-membered aromatic heterocyclic rings include, for example, pyridyl, pyrimidyl or pyrazinyl. Optional substituents for $P^1$ and $p^2$ groups include those groups $R^1$ and $R^2$ listed above When A is a bond, $P^1$ is preferably phenyl, pyridyl, pyrimidyl, pyrazinyl or pyridazinyl, preferably phenyl or pyridyl, in particular 3-pyridyl.

When A is a chain of 1 to 5 atoms, $P^1$ is preferably phenyl or pyridyl and $P^2$ is preferably phenyl or pyridyl, in particular 3-pyridyl.

When A is an optionally substituted phenyl group or an optionally substituted 5- or 6-membered aromatic heterocyclic ring, $P^1$ is preferably phenyl or pyridyl and $P^2$ is preferably phenyl or pyridyl, in particular 3-pyridyl.

Preferably $R^1$ is hydrogen or methyl.
Preferably $R^2$ is hydrogen, halogen, methyl, $CF_3$ or $OCF_3$.
Preferably $R^3$ is hydrogen.
Suitably $R^4$ is a group of formula (i). Preferably X and Y form part of a phenyl ring, that is to say one of X or Y is carbon and the other is a CH group or both of X and Y are CH groups. Most preferably $R^4$ is a group of formula (A):

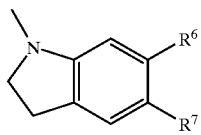

(A)

in which $R^6$ and $R^7$ are as defined in formula (i).
Suitably $R^6$ and $R^7$ groups are independently hydrogen, $C_{1-6}$ alkyl optionally substituted by one or more fluorine atoms for example $CF_3$ or $C_2F_5$, $C_{2-6}$ alkenyl, $C_{3-6}$ cycloalkyl, $C_{3-6}$ cycloalkyl$C_{1-6}$alkoxy, $C_{2-6}$ alkynyl, $C_{3-6}$ cycloalkyloxy, $C_{3-6}$ cycloalkyl-$C_{1-6}$ alkyl, $C_{1-6}$ alkylthio, $C_{3-6}$ cycloalkylthio, $C_{3-6}$ cycloalkyl-$C_{1-6}$ alkylthio, $C_{1-6}$alkoxy, hydroxy, halogen, nitro, $CF_3$, $C_2F_5$, $OCF_3$, $SCF_3$, $SO_2CF_3$, $SO_2F$, formyl, $C_{2-6}$ alkanoyl, cyano, optionally substituted phenyl or thienyl, $NR^{12}R^{13}$, $CONR^{12}R^{13}$ or $CO_2R^{14}$ where $R^{12}$, $R^{13}$ and $R^{14}$ are as defined for $R^1$; or $R^6$ and $R^7$ form part of an optionally substituted 5- or 6-membered carbocyclic or heterocyclic ring. Examples of such rings include cyclopentane and dihydrofuran rings.
Preferably $R^6$ is trifluoromethyl or halogen and $R^7$ is $C_{1-6}$ alkoxy, in particular methoxy, $C_{1-6}$alkylthio, in particular methylthio or $C_{1-6}$ alkyl in particular methyl.
Suitably n and m are independently 0, 1 or 2. Preferably n and m are both 1.
Particular compounds of the invention include:
1-[(3-Pyridyl)-3-phenyl carbamoyl]-5-methoxy-6-trifluoromethyl indoline,
1-[(4-Pyridyl)-3-phenyl carbamoyl]-5-methylthio-6-trifluoromethyl indoline,
1-[(3-Pyridyl)-3-phenyl carbamoyl]-5-methylthio-6-trifluoromethyl indoline,
1-[(3-Pyridyl)-4-phenyl carbamoyl]-5-methoxy-6-trifluromethylindoline,
1-[(4-Pyridyl)-4-phenyl carbamoyl]-5-methoxy-6-trifluoromethyl indoline,
1-[(2-Pyridyl)-3-phenyl carbamoyl]-5-methoxy-6-trifluoromethyl indoline,
1-[4-Methyl-3-(3-Pyridyl)-phenylcarbamoyl]-5-methoxy-6-trifluoromethyl indoline,
1-[3-Fluoro-5-(3-pyridyl)phenylcarbamoyl]-5-methoxy-6-trifluoromethyl indoline,
1-[2-Fluoro-5-(3-Pyridyl) phenyl carbamoyl]-5-methoxy-6-trifluoromethyl indoline,
1-(5-Phenyl pyrid-3-yl carbamoyl)-5-methoxy-6-trifluoromethyl indoline,
1-(5-Phenyl pyrid-3-yl carbamoyl)-5-methylthio-6-trifluoromethyl indoline,
1-[5-(3-Pyridyl)-pyrid-3-yl carbamoyl]-5-methoxy-6-trifluoromethyl indoline,
1-[5-(4-Trifluoromethylphenyl)-pyrid-3-yl carbamoyl]-5-methoxy-6-trifluoromethyl indoline,
1-[5-(4-Methylphenyl)-pyrid-3yl carbamoyl]-5-methoxy-6-trifluoromethyl indoline,
1-[5-(2-Thienyl)-pyrid-3-yl carbamoyl]-5-methoxy-6-trifluoromethyl indoline,
1-[5-(3-Thienyl)-pyrid-3-yl carbamoyl]-5-methoxy-6-trifluoromethyl indoline,
1-[5-(2-Pyrrolyl)-pyrid-3-yl carbamoyl)-5-methoxy-6-trifluoromethyl indoline,
1-[5-(4-Pyridyl)-pyrid-3-yl carbamoyl]-5-methoxy-6-trifluoromethyl indoline,
1-[2-(3-Pyridyl)-thiazol-4-yl carbamoyl]-5-methoxy-6-trifluoromethyl indoline,
1-[2-(2-Pyridyl)-thien-5-yl carbamoyl]-5-methoxy-6-trifluoromethyl indoline,
1-(3-Fluoro-5-(4-methyl-3-pyridyl)phenylcarbamoyl)-5-methoxy-6-trifluoromethylindoline,
1-(5-(2,6-Difluorophenyl)-3-pyridylcarbamoyl)-5-methoxy-6-trifluoromethylindoline,
6-Chloro-5-methyl-1-(4-methyl-3-(pyrid-3-yl)-phenylcarbamoyl) indoline,
1-(4-Methyl-3-(pyrid-3-yl,) phenylcarbamoyl)-5-thiomethyl-6-trifluoromethyl indoline,
1-(3-Fluoro-5-(pyrid-3-yl)phenylcarbamoyl)-5-thiomethyl-6-trifluoromethylindoline,
1-(4-Chloro-3-(pyrid-3-yl)phenylcarbamoyl)-5-methoxy-6-trifluoromethylindoline,
5-Methoxy-1-(5-methyl-(1,2-4-oxadiazol-3-yl)-phenylcarbamoyl)-6-trifluoromethyl indoline,
1-[4-Methyl-3-(4-methyl-3-pyridyl)phenylcarbamoyl]-5-methoxy-6-trifluoromethyl indoline,
1-[5-Bromo-3-(pyrid-3-yl)phenylcarbamoyl]-5-methoxy-6-trifluoromethylindoline,
1-[4-t-Butyl-3-(pyrid-3-yl)phenylcarbamoyl]-5-methoxy-6-trifluoromethylindoline,
1-[4-Methoxy-3-(pyrid-3-yl)phenylcarbamoyl]-5-methoxy-6-trifluoromethylindoline,
1-[5-Fluoro-4methoxy-3-(pyrid-3-yl)phenylcarbamoyl]-5-methoxy-6-trifluoromethylindoline,
1-[3-Bromo-4-methyl-5-(3-pyridyl)phenylcarbamoyl]-5-methoxy-6-trifluoromethylindoline,
1-[3-(4-Isoquinolyl)phenylcarbamoyl]-5-methoxy-6-trifluoromethyl indoline,
1-[5-(4-Methyl-3-pyridyl)-pyrid-3-ylcarbamoyl]-5-methoxy-6-trifluoromethylindoline,
1-[6-(3-Pyridyl)-pyrid-3-ylcarbamoyl]-5-methoxy-6-trifluoromethylindoline,
1-[5-(2-Furyl)-pyrid-3-ylcarbamoyl-5-methoxy-6-trifluoromethyl indoline,
1-[2-(Pyrazinyl)-thiazol-4-ylcarbamoyl]-5-methoxy-6-trifluoromethyl-indoline,
1-[3-(5-Pyrimidyl)phenylcarbamoyl]-5-methoxy-6-trifluoromethyl-indoline,
1-[3-(4-Methyl-3-pyridyl)phenylcarbamoyl]-5-methoxy-6-trifluoromethylindoline,
1-[5-Ethyl-3-(pyrid-3-yl)phenylcarbamoyl]-5-methoxy-6-trifluoromethylindoline,
5-Methoxy-1-[5-phenyl-3-(pyrid-3-yl)phenylcarbamoyl]-6-trifluoromethyl indoline,
6-Chloro-5-methyl-1-[4-methyl-3-(4-methyl-3-pyridyl) phenyl carbamoyl]indoline,
1-[3-(pyrid-3-ylaminocarbonyl)-phenylcarbamoyl]-5-methoxy-6-trifluoromethylindoline,
1-[3-(Pyrid-3-ylaminocarbonyl)-phenylcarbamoyl]-5-methylthio-6-trifluoromethylindoline,
1-[3-(Pyrid-4-ylaminocarbonyl)-phenylcarbamoyl]-5-methylthio-6-trifluoromethylindoline,
1-[4-(Pyrid-3-ylaminocarbonyl)-phenylcarbamoyl]-5-methylthio-6-trifluoromethyl indoline,
1-[4-(Pyrid-4-ylaminocarbonyl)-phenylcarbamoyl]-5-methylthio-6-trifluoromethyl indoline,
1-[3-(3-pyridylcarbonyl)phenylcarbamoyl]-5-methoxy-6-trifluoromethyl indoline,
1-[3-(Pyrid-3-yl-aminosulphonyl)-phenylcarbamoyl]5-methoxy-6-trifluoromethylindoline, 5-Methylthio-6-trifluoromethyl-1-[6-(pyridin-3-yloxy) pyridin-3-ylcarbamoyl)]indoline,
5-Methoxy-6-trifluoromethyl-1-[6-(pyridin-3-yloxy) pyridin-3-ylcarbamoyl]indoline,
5-Methoxy-6-trifluoromethyl-1-[4-(pyridin-4-ylmethyloxy) phenyl carbamoyl]indoline,
5-Methoxy-6-trifluoromethyl-1-[6-(pyridin-4-ylmethyloxy) pyridin-3-ylcarbamoyl]indoline,
5-Methylthio-6-trifluoromethyl-1-[4-(pyrid-4-yl-methylamino carbonyl)phenyl carbamoyl]indoline,
Trans-5-Methylthio-6-trifluoromethyl-1-{4-[2-ethenyl-(4-pyridyl)]-phenyl carbamoyl}-indoline,
5-Methylthio-6-trifluoromethyl-1-{4-[2-ethyl(4-pyridyl)] phenyl carbamoyl}indoline,
1-(1-(4-Pyridyl)-5-indolylcarbamoyl)-5-methoxy-6-trifluoromethylindoline,
5-Methoxy-6-trifluoromethyl-1-[4-(pyridin-4-ylthiomethyl) phenyl carbamoyl]indoline,
5-Methoxy-6-trifluoromethyl-1-[4-(pyridin-4-ylsulphonylmethyl) phenylcarbamoyl]indoline,
5-Methoxy-6-trifluoromethyl-1-[4-(pyridin-4-ylmethylthio) phenyl carbamoyl]indoline,
5-Methylthio-6-trifluoromethyl-1-[(6-phenoxy)-3-pyridylcarbamoyl]-indoline,
5-Methoxy-6-trifluoromethyl-1-[2-(pyridin-3-yloxy) pyridin-4-ylcarbamoyl)]indoline,
5-Methylthio-6-trifluoromethyl-1-[6-(2-methylpyridin-3-yloxy) pyridin-3-ylcarbamoyl]indoline,
5-Methylthio-6-trifluoromethyl-1-[6-(6-methylpyridin-3-yloxy)pyridin-3-ylcarbamoyl]indoline,
5-Methoxy-6-trifluoromethyl-1-[6-(pyridin-3-ylthio) pyridin-3-ylcarbamoyl]indoline,
5-Methylthio-6-trifluoromethyl-1-[4-(pyrid-3-ylmethyl) amido phenyl carbamoyl]indoline,
5-Methylthio-6-trifluoromethyl-1-[3-(pyrid-4-ylmethyl) amidophenylcarbamoyl]indoline,
5-Methylthio-6-trifluoromethyl-1-[4-(pyrid-2-ylmethyl) amidophenylcarbamoyl]indoline,
1-(1-(3-Pyridylmethyl)-5-indolylcarbamoyl)-5-methoxy-6-trifluoromethylindoline,
1-(1-(4-Pyridylmethyl)-5-indolylcarbamoyl)-5-methoxy-6-trifluoromethylindoline,
1-(1-(3-pyridyl)-5-indolylcarbamoyl)-5-methoxy-6-trifluoromethyl indoline,
5-Methylthio-6-trifluoromethyl-1-{3-[2-(3-pyridyl)thiazol-4-yl]phenylcarbamoyl}indoline,
5-Methylthio-6-trifluoromethyl-1-{4-[2-(4-pyridyl)-thiazol-4-yl]phenyl carbamoyl}indoline,
5-Methylthio-6-trifluoromethyl-1-{4-[2-(3-pyridyl)-thiazol-4-yl]phenylcarbamoyl}indoline,
1-[4-Fluoro-3-(3-pyridyl)phenylcarbamoyl]-5-methoxy-6-trifluoromethyl indoline,
1-[3-Fluoro-5-(pyrimidin-5-yl)phenylcarbamoyl]-5-methoxy-6-trifluoromethyl indoline,
1-[4-Chloro-3-(4-methyl-3-pyridyl)phenylcarbamoyl]-5-methoxy-6-trifluoromethylindoline,
1-[2,3-Dihydro-7-(pyrid-3-yl)benzofuran-5-ylcarbamoyl]-5-methoxy-6-trifluoromethyl indoline,
5-Methoxy-6-trifluoromethyl-1-[6(2-methylpyridin-3-yloxy)pyridin-3-ylcarbamoyl]indoline,
5-Methoxy-6-trifluoromethyl-1-[6(4-methylpyridin-3-yloxy)pyridin-3-ylcarbamoyl]indoline,
and pharmaceutically acceptable salts thereof.

Further preferred compounds are those of examples 83–177 and pharmaceutically acceptable salts thereof.

The compounds of the formula (I) can form acid addition salts with acids, such as conventional pharmaceutically acceptable acids, for example maleic, hydrochloric, hydrobromic, phosphoric, acetic, fumaric, salicylic, citric, lactic, mandelic, tartaric and methanesulphonic. Preferred salts are mesylate salts.

Compounds of formula (I) may also form N-oxides or solvates such as hydrates, and the invention also extends to these forms. When referred to herein, it is understood that the term 'compound of formula (I)' also includes these forms.

Certain compounds of formula (I) are capable of existing in stereoisomeric forms including enantiomers and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof.

The present invention also provides a process for the preparation of a compound of formula (I) or a pharmaceutically acceptable salt thereof, which process comprises:

(a) the coupling of a compound of formula (II);

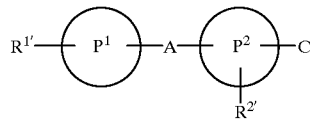

(II)

with a compound of formula (III);

$$D—R^{4'} \quad (III)$$

wherein A, $P^1$ and $P^2$ are as defined in formula (I), C and D contain the appropriate functional group(s) necessary to form the moiety —$NR^{3'}$CO when coupled, the variables $R^{1'}$, $R^{2'}$, $R^{3'}$ and $R^{4'}$ are $R^1$, $R^2$, $R^3$ and $R^4$ respectively, as defined in formula (I), or groups convertible thereto, and thereafter optionally and as necessary and in any appropriate order, converting any $R^{1'}$, $R^{2'}$, $R^{3'}$ and $R^{4'}$, when other than $R^1$, $R^2$, $R^3$ and $R^4$ respectively to $R^1$, $R^2$, $R^3$ and $R^4$, interconverting $R^1$, $R^2$, $R^3$ and $R^4$ and forming a pharmaceutically acceptable salt thereof; or (b) the coupling of a compound of formula (IV);

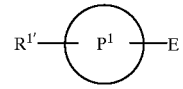

(IV)

with a compound of formula (V);

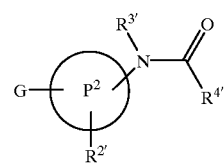

(V)

wherein $P^1$, $P^2$, $R^{1'}$, $R^{2'}$, $R^{3'}$ and $R^{4'}$ are as defined above and E and G contain the appropriate functional group(s) necessary to form the A moiety when coupled and thereafter optionally and as necessary and in any appropriate order, converting any $R^{1'}$, $R^{2'}$, $R^{3'}$ and $R^4$, when other than $R^1$, $R^2$, $R^3$ and $R^4$ respectively to $R^1$, $R^2$, $R^3$ and $R^4$, interconverting $R^1$, $R^2$, $R^3$ and $R^4$ and forming a pharmaceutically acceptable salt.

Suitable examples of groups C and D include:
(i) C is —N=C=O and D is hydrogen,
(ii) C is —NR$^{3'}$COL and D is hydrogen,
(iii) C is —NHR$^{3'}$ and D is COL, or
(iv) C is halogen and D is —CONHR$^{3'}$
wherein R$^{3'}$ is as defined above and L is a leaving group. Examples of suitable leaving groups L include halogen such as chloro, bromo, imidazole, phenoxy or phenylthio optionally substituted, for example, with halogen.

Suitable examples of a group $R^{2'}$ which are convertible to $R^2$, include alkoxycarbonyl and benzyloxy or para-methoxybenzyloxy which are converted to the group where $R^2$ is hydroxy using conventional conditions.

Interconversions of $R^1$, $R^2$ and $R^3$ are carried out by conventional procedures. For example $R^1$ halo can be introduced by selective halogenation of the ring $P^1$ using conventional conditions. It should be appreciated that it may be necessary to protect any $R^1$ to $R^3$ hydrogen variables which are not required to be interconverted.

Suitable protecting groups and methods for their attachment and removal are conventional in the art of organic chemistry, such as those described in Greene T. W. 'Protective groups in organic synthesis' New York, Wiley (1981).

Compounds of formula (II) and (III) may be prepared according to known methods or analogous to known methods, for example using the procedures described in WO 95/01976. Compounds of formula (II) in which C is NH$_2$, NO$_2$ or CO$_2$H can be prepared by reacting a compound of fomula (VI) with a compound of formula (VII):

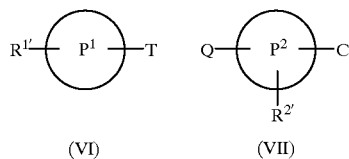

in which $R^{1'}$, $R^{2'}$, $P^1$ and $P^2$ are as defined in formula (II) and T and Q contain the apppropriate functional groups necessary to form the A group. For example
  a) when A is a bond, one of T and Q is B(OH)$_2$ or Sn(Bu)$_3$ and the other is halogen or OTf (see for example Adv. Het. Chem. 1995, 62, 306).
  b) when A is a chain, one of T and Q is an acid chloride and the other is amino, or one of T and Q is hydroxy and the other is chloro or chloromethyl; or
  c) when A is a heterocyclic ring, one of T and Q is a thioamide group and the other is BrCH$_2$C=O.

Compounds of formula (II) may be prepared according to known methods or analogous to known methods, for example
  a) from the appropriate aniline via indole formation (Nordlander [JOC, 1981, 778] or Sundberg [JOC 1984, 249] routes) followed by reduction of the indole ring using sodium cyanoborohydride. It will be appreciated that in certain cases a mixture of indoles will be formed which can be separated at this stage or at a later stage.
  b) from the appropriate ortho-methyl nitrobenzene via indole formation (Leimgruber procedure Org Syn Coll vol VII, p34) followed by reduction of the indole ring.
  c) by aromatic substitution of a suitably protected indole/indoline precursor, for example alkylthio groups maybe introduced by thiocyanation of the indoline ring followed by hydrolysis and alkylation, or
  d) From the appropriate nitrobenzene via indole formation by aromatic nucleophilic substitution (J.Med. Chem. 1990, 2089) followed by reduction of the indole using NaCNBH$_3$.

Novel intermediates of formula (III) also form part of the invention.

Suitable examples of reactions of compounds of formulae (IV) and (V) are those where E and G are the same as T and Q respectively in compounds of formulae (VI) and (VII) above. Compounds of formula (IV) are commercially available or can be prepared using standard procedures. Compounds of formula (V) can be prepared using standard procedures such as those outlined in WO 94/04533 or WO 95/01976.

Pharmaceutically acceptable salts may be prepared conventionally by reaction with the appropriate acid or acid derivative. N-oxides may be formed conventionally by reaction with hydrogen peroxide or percarboxylic acids.

Compounds of formula (I) and their pharmaceutically acceptable salts have 5HT$_{2B/2C}$ receptor antagonist activity and are believed to be of potential use fo the treatment or prophylaxis of CNS disorders such as anxiety, depression, epilepsy, obsessive compulsive disorders, migraine, Alzheimers disease, sleep disorders, feeding disorders such as anorexia and bulimia, panic attacks, withdrawal from drug abuse such as cocaine, ethanol, nicotine and benzodiazepines, schizophrenia, and also disorders associated with spinal trauma and/or head injury such as hydrocephalus. Compounds of the invention are also expected to be of use in the treatment of certain GI disorders such as IBS as well as microvascular diseases such as macular oedema and retinopathy.

Thus the invention also provides a compound of formula (I) or a pharmaceutically acceptable salt thereof, for use as a therapeutic substance, in particular in the treatment or prophylaxis of the above disorders.

The invention further provides a method of treatment or prophylaxis of the above disorders, in mammals including humans, which comprises administering to the sufferer a therapeutically effective amount of a compound of formula (I) or a pharmaceutically acceptable salt thereof.

In another aspect, the invention provides the use of a compound of formula (I) or a pharmaceutically acceptable salt thereof in the manufacture of a medicament for the treatment or prophylaxis of the above disorders.

The present invention also provides a pharmaceutical composition, which comprises a compound of formula (I) or a pharmaceutically acceptable salt thereof, and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusable solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 0.05 to 20.0 mg, for example 0.2 to 5 mg; and such unit doses may be administered more than once a day, for example two or three a day, so that the total daily dosage is in the range of about 0.5 to 100 mg; and such therapy may extend for a number of weeks or months.

When administered in accordance with the invention, no unacceptable toxicological effects are expected with the compounds of the invention.

The following Descriptions and Examples illustrate the preparation of compounds of the invention.

Description 1
6-Trifluoromethylindoline (D1)

6-Trifluoromethylindole[1] (5.27 g, 28.5 mmol) in glacial acetic acid (50 ml) was treated with sodium cyanoborohydride (3.60 g, 57.0 mmol) portionwise at room temperature with stirring. After 3 h at room temperature the reaction mixture was diluted with water (100 ml) and basified with 40% aqueous NaOH with cooling. The mixture was then extracted with dichloromethane (3×150 ml) and the combined extracts were dried ($Na_2SO_4$) and evaporated to give the title compound (4.83 g, 91%) as a brown solid.

1. A. N. Tischler and T. J. Lanza, Tet. Lett. 1986, 26, 1653.

$^1$H NMR (CDCl$_3$) δ: 3.07 (2H, t, J=8), 3.62 (2H, t, J=8), 6.80 (1H, s), 6.92 (1H, d, J=8), 7.15 (1H, d, J=8).

Description 2
5-Thiocyanato-4-trifluoromethylindoline (D2)

A mixture of 6-trifluoromethylindoline (D1) (9.7 g, 52 mmol) and potassium thiocyanate (10.09 g, 104 mmol) in methanol (200 ml) was treated with a solution of bromine (2.82 ml, 55 mmol) in methanol (35 ml) dropwise over 0.5 h at −5–0° C. The reaction mixture was allowed to warm to room temperature and stirred overnight then evaporated to dryness. The residue was partitioned between aqueous $K_2CO_3$ (100 ml) and dichloromethane (3×100 ml). The combined extracts were dried ($Na_2SO_4$) and evaporated and the residue chromatographed on silica using 2–30% ethyl acetate/petroleum ether as eluant to afford the title compound (9.1 g, 72%) as a yellow solid.

$^1$H NMR (CDCl$_3$) δ: 3.12 (2H, t, J=8), 3.72 (3H, t, J=8), 4.23 (1H, br s), 6.89 (1H, s), 7.50 (1H, s).

Description 3
Di[5-(6-trifluoromethylindolinyl)]disulphide (D3)

The thiocyanate (D2) (28.5 g, 0.116 mol) in dioxane (200 ml) and water (100 ml) was treated with aqueous ammonia (880, 200 ml) at 90° C. for 1 h. The mixture was cooled and evaporated to give a residue which was partitioned between water (300 ml) and dichloromethane (4×300 ml). The combined extracts were dried ($Na_2SO_4$) and evaporated to give the title compound (25.5 g, 100%) as a yellow solid.

$^1$H NMR(CDCl$_3$) δ: 3.03 (2H, t, J=8), 3.67 (2H, t, J=8), 4.00 (1H, br s), 6.80 (1H, s), 7.49 (1H, s).

Description 4
Di-[5-(1-acetyl-6-trifluoromethylindolinyl)]disulphide (D4)

The disulphide (D3) (26 g, 0.119 mol) in dichloromethane (300 ml) and triethylamine (47.3 ml, 0.339 mol) was treated dropwise with a solution of acetic anhydride (22.5 ml, 0.238 mol) in dichloromethane (50 ml) at 0° C. The mixture was allowed to warm to room temperature, stirred for 1 h then poured into 2.5 M aqueous HCl (400 ml). The organic layer was separated and the aqueous was further extracted with dichloromethane (200 ml). The combined organic extracts were dried ($Na_2SO_4$) and evaporated to give the title compound (29.1 g, 94%) as a yellow solid.

$^1$H NMR (CDCl$_3$) δ: 2.22 (3H, s), 3.21 (2H, t), 4.10 (2H, t), 7.68 (1H, s), 8.47 (1H, s).

Description 5
1-Acetyl-5-mercapto-6-trifluoromethylindoline (D5)

A mixture of the diacetyl disulphide (D4) (28.5 g, 54.8 mmol), triphenylphosphine (20.85 g, 79.5 mmol) and conc. aqueous HCl (1 ml) in dioxane (300 ml) and water (75 ml) was heated at reflux for 1.5 h. The reaction mixture was cooled and evaporated to a residue which was partitioned between dichloromethane (300 ml) and 1% aqueous NaOH (300 ml). The organic phase was further extracted with 1% aqueous NaOH (200 ml) and the combined aqueous fractions carefully acidified and extracted with dichloromethane (3×300 ml). The combined organic extracts were dried ($Na_2SO_4$) and evaporated to afford the title compound (26 g, 91%) as a yellow solid.

$^1$H NMR (CDCl$_3$) δ: 2.24 (3H, s), 3.20 (2H, t), 3.68 (1H, m), 4.11 (2H, t), 7.22 (1H, s), 8.51 (1H, s).

Description 6
1-Acetyl-5-methylthio-6-trifluoromethylindoline (D6)

A mixture of the thiol (D5) (26 g, 99 mmol), anhydrous $K_2CO_3$ (15.12 g, 109 mmol) and iodomethane (18.6 ml, 300 mmol) in dry DMF (100 ml) was heated at 80° C. for 1 h. The reaction mixture was cooled, evaporated in vacuo and partitioned between water (200 ml) and dichloromethane (3×200 ml). The combined organics were washed with water (400 ml), dried ($Na_2SO_4$) and evaporated to yield the title compound (26.3 g, 97%) as a yellow oil.

$^1$H NMR (CDCl$_3$) δ: 2.22 (3H, s), 2.49 (3H, s), 3.24 (2H, t, J=8), 4.12 (2H, t, J=8), 7.23 (1H, s), 8.51 (1H, s).

Description 7
5-Methylthio-6-trifluoromethylindoline (D7) Method (a)

The acetyl indoline (D6) (26.3 g, 95 mmol) was treated with NaOH (30 g, 750 ml) in water (150 ml) and ethanol (200 ml) at reflux for 1.5 h. The reaction mixture was cooled, diluted with water (200 ml) and most of the ethanol evaporated in vacuo. The remaining mixture was extracted with dichloromethane (3×200 ml) and the combined extracts were dried ($Na_2SO_4$) and evaporated to afford the title compound (21.9 g, 99%) as a yellow oil.

¹H NMR (CDCl₃) δ: 2.41 (3H, s), 3.07 (2H, t), 3.63 (2H, t), 3.90 (1H, br s), 6.88 (1H, s), 7.30 (1H, s).
Method (b)

A stirred solution of potassium thiocyanate (38.6 g, 0.39 mol) in methanol (470 ml) at −2° C. under argon was treated dropwise over 10 minutes with bromine (10.3 ml, 0.195 mol) giving a yellow precipitate. The reaction mixture was stirred at 0° C. for a further 15 minutes, then treated with a solution of 6-trifluoromethylindoline (D1) (33.2 g, 0.177 mol) in methanol (320 ml) and allowed to warm to room temperature and stir for 4 h. A solution of potassium hydroxide (49.5 g, 0.88 mol) in water (300 ml) was added in one portion, causing the temperature to rise to 43° C. and a brown solution to be produced. The mixture was stirred at 43–45° C. for 25 minutes, then cooled to 12° C. and treated with iodomethane (10.9 ml, 0.177 mol). The resulting mixture was allowed to warm to room temperature and stirred for 1.5 h, then concentrated in vacuo to approx. 350 ml volume. The residual aqueous mixture was extracted with dichloromethane (2×400 ml) and the combined extract dried (Na₂SO₄) and concentrated in vacuo to give a brown oil (43 g), which was chromatographed on silica gel eluting with dichloromethane to afford the title compound (D7) as a light brown solid (25.3 g, 61%) with spectral properties identical to those described above.

Description 8
1-Methoxy-4-nitro-2-trifluoromethylbenzene (D8)

Sodium (11.78 g, 0.512 mol) was dissolved in dry methanol (1 l) and to the resulting solution was added a solution of 1-chloro-4-nitro-2-trifluoromethyl-benzene (96.22 g, 0.427 mol) in methanol (100 ml). The reaction mixture was refluxed for 3 h then cooled and evaporated in vacuo. The residue was partitioned between water (500 ml) and dichloromethane (3×400 ml). The combined organic extracts were dried (Na₂SO₄) and evaporated to give the title compound (93.76 g, 99%) as a white solid.

¹H NMR (CDCl₃) δ: 4.05 (3H, s), 7.12 (1H, d), 8.45 (1H, dd), 8.52 (1H, d).

Description 9
(5-Methoxy-2-nitro-4-trifluoromethylphenyl)acetonitrile (D9)

A mixture of 1-methoxy-4-nitro 2-trifluoromethylbenzene (D8) (93 g, 0.421 mol) and 4-chlorophenoxyacetonitrile (77.55 g, 0.463 mol) in dry DMF (500 ml) was added dropwise over 0.75 h to a stirred solution of KOᵗBu (103.85 g, 0.927 mol) in dry DMF (400 ml) at −10° C. After complete addition the resulting purple solution was maintained at −10° C. for 1 h then poured into a mixture of ice/water (1.5 l) and 5 M aqueous HCl (1.5 l). The resulting mixture was extracted with dichloromethane (3×1l). The combined extracts were washed with water (3 l), dried (Na₂SO₄) and evaporated under reduced pressure. The residue was chromatographed on silica using 10–40% ethyl acetate/petroleum ether as eluant to give the crude product which was recrystallised from ethyl acetate/petroleum ether to afford the title compound (85.13 g, 78%) as a white solid. Mp 103–104 ° C.

¹H NMR (CDCl₃) δ: 4.10 (3H, s), 4.37 (2H, s), 7.34 (1H, s), 8.53 (1H, s).

Description 10
5-Methoxy-6-trifluoromethylindole (D10)

(5-Methoxy-2-nitro-4-trifluoromethylphenyl)acetonitrile (D9) (85 g, 0.327 mol) in ethanol/water (9:1, 1.6 l) and glacial acetic acid (16 ml) was hydrogenated over 10% palladium on carbon (50 g) at 50 psi for 0.5 h at room temperature. The reaction mixture was filtered and evaporated in vacuo. The residue was partitioned between aqueous K₂CO₃ (1 l) and dichloromethane (2×1 l) and the combined organic extract was dried (Na₂SO₄) and evaporated to afford the title indole (67.63 g, 96%) as a grey solid.

¹H NMR (CDCl₃) δ: 3.94 (3H, s), 6.53 (1H, m), 7.21 (1H, s), 7.32 (1H, m), 7.64 (1H, s), 8.25 (1H, br s).

Description 11
5-Methoxy-6-trifluoromethylindoline (D11)

The indole (D10) (67.63 g, 0.315 mol) was treated with sodium cyanoborohydride (40 g, 0.637 mol) in glacial acetic acid (500 ml) as in the method of Description 1 to afford the title indoline (67.73 g, 99%) as an off-white solid.

¹H NMR (CDCl₃) δ: 3.07 (2H, t), 3.58 (2H, t), 3.67 (1H, br s), 3.83 (3H, s), 6.83 (1H, s), 6.88 (1H, s).

Description 12
3-(4-Pyridyl) aniline (D12)

3-Bromoaniline (0.24 ml, 2.2 mmol) and sodium carbonate (0.70 g, 6.6 mmol) were suspended in a mixture of 1,2-dimethoxyethane (16 ml) and water (4 ml). The reaction mixture was then treated with 4-pyridyl boronic acid (0.27 g, 2.2 mmol), and flushed with Argon. Tetrakis (triphenylphosphine)-palladium (0) (0.35 g) was then added, and the mixture was heated to reflux under Argon for 24 hours. The reaction mixture was allowed to cool after which it was partitioned between dichloromethane and water. The aqueous layer was again extracted with dichloromethane. The combined extracts were then dried (Na₂SO₄) and concentrated in vacuo to afford a pale yellow solid (0.35 g). This was chromatographed on silica gel eluting with ethyl acetate to afford the title compound as a white solid (0.15 g, 41%).

¹H NMR (200 MHz, CDCl₃) δ(ppm): 8.63 (dm, 2H), 7.45 (dm, 2H), 7.35 (t, 1H), 7.0 (dm, 1H), 6.91(m, 1H), 6.75 (dm, 1H), 3.75 (b, 2H)

Description 13
3-(3-Pyridyl)aniline (D13)

A mixture of 3-bromopyridine (2.9 ml, 4.74 g, 30 mmol), 3-aminophenyl boronic acid (4.63 g, 30 mmol), sodium carbonate (10 g, 90 mmol) and tetrakis (triphenylphosphine) palladium (0) (0.9 g) in 1,2-dimethoxyethane—water (150 ml–50 ml) was heated to reflux under argon for 12 h. The mixture was concentrated then partitioned between ethyl acetate/dilute brine. The organic extract was dried and evaporated affording a brown gum (6 g). Chromatography on silica eluting with 50% ethyl acetate—60/80 petroleum ether then ethyl acetate afforded the product as a yellow crystalline solid (4.8 g, 95%).

¹H NMR (200 MHz, CDCl₃) 3.8 (2H, 6s), 6.70 (1H, dm), 6.85 (1H, m), 6.95 (1H, m), 7.25 (1H, t), 7.35 (1H, m) 7.85 (1H, m), 8.60 (1H, dd), 8.85 (1H, d).

Description 14
1-(5-Bromo-pyrid-3-yl carbamoyl)-5-methoxy-6-trifluromethyl-indoline (D14)

A solution of 5-bromo-pyrid-3-yl acyl azide (3.16 g, 13.9 mmol) in toluene (500 ml) was heated to reflux under argon for 1 h. The solution was allowed to cool to room temperature then added to a solution of 5-methoxy-6-trifluoromethyl indoline (2.7 g, 12.5 mmol) in dichloromethane (200 ml). The mixture was set aside in the fridge for 1 h, then filtration and drying afforded the title compound as a white solid (4.62 g, 89%), mp 220–222° C.

¹H NMR (D⁶-DMSO) 3.30 (2H, t, J), 3.85 (3H, S), 4.20 (2H, t), 7.20 (1H, S), 8.10 (1H, S), 8.35 (2H, m), 8.75 (1H, S), 8.95 (1H, S).

Description 15
2-(3-Pyridyl)-thiazole-4-carbonyl azide (D5)

A suspension of 2-(3-pyridyl)-thiazole-4-carboxylic acid (0.824 g, 4 mmol) in dichloromethane-chloroform (30 ml–15 ml) was treated with triethylamine (0.75 ml, 0.5 g, 5 mmol) and then iso-butyl chloroformate (0.65 ml, 0.68 g, 5 mmol). After 1 h the mixture was evaporated to dryness and the residue suspended in THF (30 ml) and a solution of sodium azide (0.46 g, 7 mmol) in water (10 ml) was added. After 1 h, the mixture was concentrated (rotary evaporator) and partitioned between dichloromethane and brine. The organic extract was washed with half-saturated brine, dried, and evaporated. Trituration with petroleum ether, filtration, and drying in vacuo (CAUTION—no heating) afforded the title compounds as a brown solid (0.37 g, 40%).

Description 16

2-(2-Pyridyl)-thiophene-5-carbonyl azide (D16)

This was prepared in 45% yield by the same method as for Description 15.

Description 17

1-(3-Fluoro-5-iodophenylcarbamoyl)-5-methoxy-6-trifluoromethylindoline (D17)

A mixture of 3-fluoro-5-iodoaniline (0.47 g, 1.98 mmol) and 1,1'-carbonyl diimidazole (0.33 g, 2 mmol) in dichloromethane (40 ml) was stirred at room temperature for 1 h, then evaporated to dryness. To the residue was added dimethylformamide (DMF,10 ml) and a solution of 5-methoxy-6-trifluoromethylindoline (D11, 0.44 g, 2 mmol) in DMF (5 ml). The mixture was heated at 80° C. overnight, then cooled and poured into water. The precipitate was filtered off, washed with water and dried. The crude product was chromatographed on silica gel and eluted with dichloromethane. Eluted product was recrystallised from dichloromethane to give tie title compound (0.38 g, 40%), Mp. 221–4° C.

$^1$H NMR (d$_6$DMSO) δ: 3.27 (2H, t, J=8), 3.84 (3H, s), 4.15 (2H, t, J=8), 7.20 (1H, s), 7.27 (1H, d, J=7), 7.57 (1H, d, J=12), 7.84 (1H, s), 8.10 (1H, s), 8.78 (1H, s).

MS (EI) m/z=480 (M$^+$), C$_{17}$H$_{13}$N$_2$O$_2$F$_4$I requires M=480

Description 18

Ethyl 5-(2,6-difluorophenyl)nicotinate (D18)

A mixture of (2,6-difluorophenyl)tributyltin (1.18 g, 2.9 mmol), ethyl 5-bromonicotinate (0.69 g, 3 mmol) and tetrakis (triphenylphosphine) palladium (0) (0.10 g) in xylene (10 mL) was heated under reflux for 24 h, then cooled, filtered and evaporated. The residue was chromatographed on silica gel eluted with 20% ethyl acetate/petrol to give the title compound (0.64 g, 84%).

$^1$H NMR (CDCl$_3$) δ: 1.43 (3H, t, J=7), 4.44 (2H, q, J=7), 7.06 (2H, t, J=7), 7.39 (1H, quintet, J=7), 8.42 (1H, s), 8.88 (1H, s), 9.23 (1H, s)

MS (API): m/z=264 (MH$^+$), C$_{14}$H$_{11}$NO$_2$F$_2$ requires M+1=264

Description 19

5-(2,6-Difluorophenyl)nicotinoyl hydrazide (D19)

A mixture of ester (D18, 0.64 g, 2.4 mmol) and 98% hydrazine hydrate (1 mL) in methanol (10 mL) was heated under reflux overnight, then cooled in ice. The precipitate was filtered off. The filtrate was evaporated and the residue was triturated with water before combining with the initial precipitate. The crude product was washed with ether and dried in vacuo to give the title compound (0.50 g, 84%).

$^1$H NMR (d$_6$ DMSO) δ: 4.60 (2H, s), 7.29 (2H, t, J=7), 7.57 (1H, quintet, J=7), 8.28 (1H, s), 8.80 (1H, s), 9.03 (1H, s), 10.05 (1H, s).

MS (API): m/z=250 (MH$^+$), C$_{12}$H$_9$N$_3$OF$_2$ requires M+1=250

Description 20

5-(2,6-Difluorophenyl)nicotinoyl azide (D20)

To a suspension of hydrazide (D19, 0.50 g, 1.99 mmol) in concentrated hydrochloric acid (3 mL) and water (2 mL) at −5° C. was added dropwise a solution of sodium nitrite (0.14 g, 2.0 mmol) in water (2 ml). The mixture was stirred at −5° C. for 0.5 h, then a solution of potassium carbonate (2.3 g) in water (25 ml) was added cautiously. The precipitate was filtered off, washed with water and dried in vacuo at room temperature to give the title compound (0.48 g, 93%).

$^1$H NMR (CDCl$_3$) δ: 7.05 (2H, t, J=7), 7.40 (1H, quintet, J=7), 8.41 (1H, s), 8.93 (1H, s), 9.22 (1H, s)

MS (API) 261 (MH$^+$), 233 (MH$^+$—N$_2$)

Description 21

Phenyl N-(3-Bromo-5-(pyrid-3-yl)phenyl)carbamate (D21)

The tide compound was prepared from 3-Bromo-5-(pyrid-3-yl)aniline using the method of Description 67.

$^1$H NMR 250 MHz CDCl$_3$ δ: 7.1–7.9 (m, 9H), 8.6–8.7 (br, 1H, Ar), 8.8–8.9 (br, 1H, Ar)

Description 22

Phenyl N-[4-t-Butyl-3-(pyrid-3-yl)phenyl]carbamate (D22)

The title compound (0.18 g, 68%) was prepared from 4-t-butyl-3-(pyrid-3-yl)aniline (0.175 g, 0.00077 mole) using the method of Description 67.

$^1$H NMR (200 MHz, CDCl$_3$) δ: 1.18 (9H, s), 7.02–7.65 (11H, m), 8.49–8.62 (2H,m)

Description 23

Phenyl N-[4-Methoxy-3-(pyrid-3-yl)phenyl]carbamate (D23)

The title compound (0.48 g, 75%) was prepared from 4-methoxy-3-(pyrid-3-yl)aniline (0.40 g, 0.002 mole) using the method of Description 67.

$^1$H NMR (200 MHz, CDCl$_3$) δ: 3.80 (3H, s), 6.90–7.57 (10H, m), 7.88 (1H, dt), 8.56 (1H, dd), 8.78 (1H, d)

Description 24

Phenyl N-[5-Fluoro-4-methoxy-3-(pyrid-3-yl)phenyl] carbamate (D24)

The title compound (0.48 g, 79%) was prepared from 5-fluoro-4-methoxy-3-(pyrid-3-yl)aniline (0.40 g, 0.0018 mole) using the method of Description 67.

$^1$H NMR (200 MHz, CDCl$_3$) δ: 3.75 (3H, s), 7.01–7.67 (8H, m), 7.82–8.08 (2H, m), 8.64 (1H, d), 8.80 (1H, s).

Description 25

1-(3,5-Dibromo-4-methylphenylcarbamoyl)-5-methoxy-6-trifluoromethylindoline (D25)

The title compound was prepared by the method of Example 1, from 3,5-dibromo-4-methylaniline (2.64 g, 10 mmol), 1,1'-carbonyldiimidazole (1.64 g, 10 mmol) and 5-methoxy-6-trifluoromethylindoline (D11) (2.2 g, 10 mmol). Crude product was recrystallised from DMSO/water and washed with methanol and ether, to give the title compound (2.64 g, 52%), mp >250° C.

NMR (d$_6$-DMSO) δ: 2.43 (3H, s), 3.26 (2H, t, J=8), 3.84 (3H, s), 4.14 (2H, t, J=8), 7.20 (1H, s), 7.96 (2H, s), 8.10 (1H, s), 8.72 (1H, s).

MS (API) 507 (MH$^+$, $^{79}$Br$_2$), 509 (MH$^+$, $^{79}$Br$^{81}$Br), 511 (MH$^+$, $^{81}$Br$_2$)

Description 26

1-[5-Bromo-(3-pyridylcarbamoyl)]-5-methoxy-6-trifluoromethyl indoline (D26)

5-Bromo-3-pyridylcarbonylazide (3.7 g, 16 mmoles) was heated under reflux in dry toluene (100 ml) for 1 hr. After cooling the resulting solution of isocyanate was treated with a solution of 5-methoxy-6-trifluoromethyl indoline (D11) (3.5 g, 16 mmoles) in dichloromethane (600 ml) and stirred overnight. The mixture was concentrated in vacuo and the residue triturated with diethyl ether. Filtration and washing with more diethyl ether gave the title compound (D26) (5.4 g, 81%).

$^1$H NMR (DMSO-d$^6$) δ: 3.30 (2H, t, J=8 Hz), 3.83 (3H, s), 4.18 (2H, t, J=8 Hz), 7.20 (1H, s), 8.10 (1H, s), 8.30–8.35 (1H, m), 8.71 (1H, s), 8.92 (1H, s)

Description 27
Phenyl N-[6-(Pyrid-3-yl)pyrid-3-yl]carbamate (D27)

The title compound was prepared as in the method of description 67 from the corresponding aniline. This gave the title compound (0.66 g, 100%)

M.S. (API) found m/z 292 (MH$^+$), $C_{17}H_{13}N_3O_2$ requires 292

Description 28
Phenyl-N-[3-(4-methylpyrid-3-yl)phenyl]carbamate (D28)

The title compound was prepared as in the method of description 67 from the corresponding aniline. This gave the title compound (0.8 g, 100%)

NMR (CDCl$_3$) δ: 2.29 (3H, s), 7.10–7.40 (11H, m), 8.42–8.49 (2H, m)

Description 29
3-(5-Pyrimidyl)-aniline (D29)

This was prepared from 5-bromopyrimidine and 3-aminophenyl boronic acid in 84% yield by the same method as for Description 12.

$^1$H NMR (CDCl$_3$) 3.80 (2H., bs), 6.80 (1H, dd), 6.90 (1H, m), 7.00 (1H, d), 7.30 (2H, m), 8.95 (2H, s), 9.20 (1H, s).

Description 30
Phenyl N-[3-ethyl-5-(pyrid-3-yl)phenyl]carbamate (D30)

The title compound (0.276 g, 0.87 mmol) was prepared by the methodology of description 67, using 3-ethyl-5-(pyrid-3-yl)aniline, phenyl chloroformate (0.13 ml, 0.96 mmol) and triethylamine (0.13 ml, 0.96 mmol) in dichloromethane (10 ml)

$^1$H NMR 250 MHz CDCl$_3$ δ: 8.78 (s, 1H, Ar), 8.51 (m, 1H, Ar), 7.08–7.92 (m, 5H, Ar), 2.51 (t, 2H, CH$_2$), 1.20 (q, 3H, Me)

Description 31
Phenyl N-[5-phenyl-3-(pyrid-3-yl)phenyl]carbamate

The title compound (0.289 g, 100%) was prepared by methodology of description 67 using 5-phenyl-3-(pyrid-3-yl) aniline (0.194 mg, 0.79 mmol), phenyl chloroformate (0.12 ml, 0.87 mmol) and triethylamine (0.12 ml, 0.81 mmol) in DCM (10 ml)

$^1$H NMR 250 MHz CDCl$_3$ δ: 8.92 (br, 1H, Ar), 8.65 (d, 1H, Ar), 7.95 (d, 1H, Ar), 7.82 (s, 1H, Ar), 7.72–7.12 (m, 8H, Ar)

Description 32
3-(3-Nitrobenzoylamino)-pyridine

A solution of 3-aminopyridine (2 g, 20 mmol) in tetrahydrofuran (100 ml) was treated at 0° C. with triethylamine (3 ml, 2.2 g, 22 mmol) and then a solution of 3-nitrobenzoyl chloride (3.7 g, 20 mmol) in tetrahydrofuran (50 ml). After 0.5 h the reaction mixture was diluted with water (400 ml) and set aside in the fridge for 3 days. Filtration and drying afforded the title compound as a purple crystalline solid (4.82 g, 99%).

$^1$H NMR (D6-DMSO) 7.40 (1H, m), 7.85 (1H, t, J 8 Hz), 8.20 (1H, d, J 8 Hz), 8.30–8.50 (3H, m), 8.80 (1H, s), 8.95 (1H, d, J 2 Hz).

Description 33
3-(3-Aminobenzoylamino)-pyridine

A solution of 3-(3-nitrobenzoylamino)-pyridine (2 g, 8.23 mmol) in ethanol (200 ml) was treated with 10% palladium on charcoal (0.5 g) and hydrogenated at atmospheric pressure for 4 h. Filtration and evaporation afforded the product as a white solid (1.51 g, 86%)

$^1$H NMR (D6-DMSO) 5.40 (2H, bs), 6.75 (1H, d, J 8 Hz), 7.0–7.2 (3H, m), 7.40 (1H, m), 8.15 (1H, d, J 8 Hz), 8.30 (1H, m), 8.90 (1H, d, J 2 Hz).

Description 34
5-Methylthio-6-trifluoromethyl-1-(3-ethoxycarbonyl phenyl carbamoyl)indoline To a stirred solution of carbonyl diimidazole (1.782 g, 11 mmol) in dichloromethane (20 ml) was added dropwise a solution of ethyl 3-amino benzoate (1.65 g, 10 mml) in dichloromethane (20 ml). After 1 hour the reaction mixture was evaporated under reduced pressure before being treated with 5-methylthio-6-trifluoromethyl indoline (2.33 g, 10 mmol) and dimethylformamide (30 ml) and heated to 100° C. After 1 hour the reaction mixture was cooled and water added forming a yellow precipitate. This was filtered and dried to give the product as a yellow solid (4.19 g, 99%), m.p. 195–7° C.

$^1$H NMR (DMSO) δ: 8.85 (1H, s); 8.2 (2H, d, J6 Hz); 7.9 (1H, d, J7 Hz); 7.6 (1H, d, J7 Hz); 7.4 (2H, t, J6 Hz); 4.3 (2H, q, J7 Hz); 4.2 (2H, t, J8 Hz); 3.25 (2H, t, J8 Hz); 2.5 (3H, s); 1.3 (3H, t, J7 Hz).

Description 35
5-Methylthio-6-trifluoromethyl-1-(4-ethoxycarbonyl phenyl carbamoyl) indoline This was made in the same manner as Description 34 using ethyl-4-amino benzoate to give the product as a yellow solid (3.948 g, 93%), m.p. >200° C.

$^1$H NMR (DMSO) δ: 8.95 (1H, s); 8.2 (1H, s); 7.9 (2H, d, J7 Hz); 7.75 (2H, d, J7 Hz); 7.4 (1H, s), 4.2 (4H, m); 3.25 (2H, t, J8 Hz); 2.5 (3H, s); 1.3 (3H, t, J7 Hz)

Description 36
5-Methylthio-6-trifluoromethyl-1-(3-carboxy phenyl carbamoyl)indoline To a suspension of 5-methylthio-trifluoromethyl-1-(3-ethoxy carbonyl phenyl carbamoyl) indoline (3 g, 7.1 mmol) in ethanol (30 ml) was added aqueous sodium hydroxide solution (5M) (7.1 ml, 35.5 mmol) and heated gently for 2 hours. It was then allowed to cool and acidified with aqueous hydrochloric acid (5M) forming a white precipitate which was filtered and dried to yield the product as a white solid (2.324 g, 83%), mp >200° C.

$^1$H NMR (DMSO) δ: 12.95 (1H, s); 8.85 (1H, s); 8.2 (2H, s); 7.85 (1H, d, J7 Hz); 7.6 (1H, d, J7 Hz); 7.4 (2H, t, J7 Hz); 4.2 (2H, t, J6 Hz); 3.25 (2H, t, J6 Hz); 2.5 (3H, s)

Description 37
5-Methylthio-6-trifluoromethyl-1-(4-carboxy phenyl carbamoyl) indoline This was made in the same manner as Description 36 using 5-methylthio-6-trifluoromethyl-1-(4-ethoxycarbonyl phenyl carbamoyl) indoline to give the product as a pale green solid (2.455 g, 88%), mp >200° C.

$^1$H NMR (DMSO) δ: 1.27 (1H, s); 8.9 (1H, s); 8.2 (1H, s); 7.9 (2H, d, J7 Hz); 7.7 (2H, d, J7 Hz); 7.4 (1H, s); 4.2 (2H, t, J8 Hz); 3.75 (2H, t, J8 Hz); 2.5 (3H, s)

Description 38
3-(Pyrid-3-ylaminosulphonyl)-nitrobenzene

To a stirred solution of 3-aminopyridine (2 g, 21.3 mmol) in pyridine (100 ml) was added 3-nitrobenzene sulphonyl chloride (4.43 g, 20 mmol) and the mixture was heated to 50° C. for 3 hours. After cooling it was partitioned between ethyl acetate and water and the organic washed with water (×2) and half saturated aqueous sodium chloride solution, separated, dried and evaporated to give a crude yield of 4.96 g. It was then triturated with dichloromethane and sonicated for 0.25 hours before being filtered and dried to give the product as a pink solid (4.279 g, 72%)

$^1$H NMR (DMSO) δ: 10.9 (1H, s); 8.45 (2H, d, J7 Hz); 8.3 (2H, s); 8.15 (1H, d, J7 Hz); 7.9 (1H, t, J7 Hz); 7.55 (1H, d, J7 Hz); 7.3 (1H, q, J5 Hz).

Description 39
3-(Pyrid-3-ylaminosulphonyl)-aminobenzene

To a solution of 3-(pyrid-3-ylaminosulphonyl)-nitrobenzene (4.279 g, 15.3 mmol) in ethanol (500 ml)/ dimethylformamide (50 ml) was added 10% palladium catalyst on charcoal (1 g) and the reaction mixture was hydrogenated at atmospheric pressure for 2 hours. The reaction mixture was then filtered through kieselguhr before being evaporated under reduced pressure to give the product as a white solid (3.749 g, 98%)

$^1$H NMR (DMSO) δ: 10.4 (1H, s); 8.25 (1H, s); 8.2 (1H, d, J5 Hz); 7.5 (1H, d, J7 Hz); 7.3 (1H, q, 5 Hz); 7.15 (1H, t, J7 Hz); 6.95 (1H, s); 6.8 (1H, d, J7 Hz); 6.7 (1H, d, J7 Hz); 5.6 (2H, s)

Description 40

3-(3-Nitrobenzoyl)pyridine

The title compound (1.55 g, 25%) was prepared using the method of Langhals et al (Liebigs Ann. Chem. 1982, 930–949), and purified by flash column chromatography on silica gel, eluting with 30% ethyl acetate 60–80° petroleum ether $^1$H NMR (200 MHz, CDCl$_3$) δ: 7.40–7.60 (1H, m); 7.75 (1H, t), 7.98–8.23 (2H, m), 8.50 (1H, dd), 8.59–8.70 (1H, m), 8.90 (1H, dd), 9.01 (1H, d)

Description 41

3-(3-Aminobenzoyl)pyridine 3-(3-Nitrobenzoyl)pyridine (1.55 g, 0.006 mole) was suspended in ethanol (35 ml) and treated portionwise with a solution of tin (11) chloride (4.56, 0.024 mmole) in conc. HCl (7 ml). The reaction mixture was stirred at 50° C. for 2 hours. After allowing to cool to room temperature, water (50 ml) was added and the mixture basified with 10% aqueous sodium hydroxide, extracted into ethyl acetate, dried (Na$_2$SO$_4$) and evaporated in vacuo to afford the title compound (1.14 g, 85%) as a pale oil $^1$H NMR (200 MHz; CDCl$_3$) δ: 3.90 (2H, s), 6.81–7.03 (1H, m), 7.03–7.20 (2H, m), 7.28 (1H, t), 7.39–7.59 (1H, m), 8.14 (1H, dd), 8.80 (1H, dd), 9.01 (1H, s)

Description 42

Trans-4-[2-ethenyl-(4-pyridyl)]-nitrobenzene (D42)

A solution of (4-nitrobenzyl)triphenylphosphonium bromide (32 g, 66 mmol in ethanol (100 ml) was treated with sodium methoxide (3.6 g, 66 mmol). After 0.75 h pyridine-4-carboxaldehyde (5.04 ml, 52.8 mmol) was added and the mixture stirred for 16 h. The mixture was subjected to an ethyl acetate/dilute brine workup. Drying, evaporation and chromatography afforded the product as an equal mixture of isomers. Recrystallisation from ethyl acetate petroleum ether afforded the tide compound (single isomer) as a yellow solid (2.72 g, 17%).

$^1$H NMR (D6-DMSO) 7.50 (1H, d), 7.65 (2H, d), 7.70 (1H, d), 7.95 (2H, d), 8.30 (2H, d), 8.65 (2H, d).

Description 43

Trans-4-[2-ethenyl-(4-pyridyl)]-aniline (D43)

A suspension of trans-4-[2-ethenyl-(4-pyridyl)]-nitrobenzene (D42) (0.5 g, 2.2 mmol) in ethanol (30 ml) at 50° C. was treated with a solution of stannous (II) chloride (1.25 g, 6.6 mmol) in concentrated hydrochloric acid (2 ml). The mixture was maintained at 50° C. overnight then evaporated to dryness. The residue was partitioned between ethyl acetate and 5M aqueous sodium hydroxide solution. Drying and evaporation afforded a yellow solid which was triturated with ether-petroleum ether (1:1) affording the title compound as a yellow solid (100 mg. 23%).

$^1$H NMR (D6-DMSO) 5.50 (2H, bs), 6.60 (2H, d), 6.85 (1H, d), 7.30–7.50 (5H, m), 8.45 (2H, d)

Description 44

4-Nitro-2-(pyridin-3-yloxy)pyridine-N-oxide (D44)

Sodium hydride (0.27 g of an 80% dispersion in oil, 9 mmol) was added to a solution of 3-hydroxypyridine (0.854 g, 9 mmol) in THF (3 ml) at 0° C. The mixture was then stirred for 1 h at room temperature before 2-chloro-4-nitropyridine-N-oxide* (2 g, 9 mmol) was added. The resulting solution was heated at reflux for 16 h, cooled, poured into water (100 ml) and extracted with dichloromethane (3×100 ml). The combined extracts were dried (Na$_2$SO$_4$) and evaporated. The residue was chromatographed on silica using ethyl acetate as eluant to afford the title compound (1.74 g, 83%) as a solid.

* G. C. Finger and L. D. Stair, *J. Am. Chem. Soc.*, 81, 2674 (1959)

$^1$H NMR (250 MHz; CDCl$_3$) δ: 7.42 (2H, m), 7.83 (1H, m), 8.00 (1H, dd, J=8 Hz, 2 Hz), 8.42 (1H, d, J 8 Hz), 8.51 (1H, m), 8.59 (1H, m).

Description 45

4-Amino-2-(pyridin-3-yloxy)pyridine (D45)

4-Nitro-2-(pyridin-3-yloxy)pyridine-N-oxide (D44) (1 g, 4.3 mmol) in acetic acid (75 ml) was treated with iron powder (1.2 g, 21.4 mmol) at room temperature. After 2 h the mixture was concentrated under reduced pressure and partitioned between 2M aq NaOH (100 ml) and dichloromethane (4×100 ml). The combined extracts were dried and evaporated to a white crystalline solid (0.75 g, 93%) which was used without further purification.

$^1$H NMR (250 MHz; CDCl$_3$) δ: 4.25 (2H, br), 6.17 (1H, d, J 2 Hz), 6.33 (1H, dd, J 7 Hz, 2 Hz), 7.26 (1H, s), 7.32 (1H, dd, J 8 Hz, 5 Hz), 7.48 (1H, m, J 8 Hz), 7.82 (1H, d, J 7 Hz), 8.42 (1H, m, J 5 Hz), 8.48 (1H, d, J 2 Hz).

Description 46

5-Nitro-1-(3-pyridylmethyl)indole (D46)

5-Nitroindole (0.49, 3 mmol) was treated with sodium hydride (0.198 g, 6.6 mmol) in dry dimethylformamide (20 ml). After 15 min at room temperature, 3-picolyl chloride hydrochloride (0.49 g, 3 mmol) was added and the mixture was stirred at room temperature for 24 h, then poured into water. The precipitate was filtered off, washed with water and dried to give the title compound (0.67 g, 88%), m.p. 131–4° C.

$^1$H NMR (CDCl$_3$) δ: 5.40 (2H, s), 6.75 (1H, d, J=3), 7.2–7.4 (4H, m), 8.09 (1H, dd, J=8,2), 8.52 (1H, s), 8.57 (1H, d, J=4), 8.61 (1H, d, J=2).

MS(API) m/z=254(MH$^+$)

Description 47

5-Nitro-1-(4-pyridylmethyl)indole (D47)

The title compound was prepared by the method of Description 46 using 4-picolyl chloride hydrochloride. Yield 87%, m.p. 134–136° C.

$^1$H NMR (CDCl$_3$) δ: 5.41 (2H, s), 6.80 (1H, d, J=3), 6.93 (2H, d, J=7), 7.23 (1H, d, J=8), 7.30 (1H, d, J=3), 8.10 (1H, dd, J=8,2), 8.57 (2H, d, J=7), 8.64 (1H, d, J=2) MS(API) m/z=254(MH$^+$)

Description 48

5-Amino-1-(3-pyridylmethyl)indole (D48)

To a stirred suspension of nitroindole (D46) (0.63 g, 2.5 mmol), and iron powder (0.41 g, 7.2 mmol) in methanol (20 ml) was added a solution of ammonium chloride (0.66 g, 12.4 mmol) in water (13 ml). The mixture was then heated under reflux for 12 h, then filtered while hot and evaporated. The residue was diluted with water and extracted with dichloromethane. The organic extract was washed with brine, dried and evaporated to give the title compound (0.40 g, 72%) as a gum.

$^1$H NMR (CDCl$_3$) δ: 5.25 (2H, s), 6.38 (1H, d, J=3), 6.63 (1H, dd, J=8,2), 6.94 (1H, d, J=2), 7.03 (1H, d, J=8), 7.05 (1H, d, J=3), 7.18 (1H, dd, J=7,4), 7.29 (1H, d, J=7), 8.52 (2H, broad s).

MS(API) m/z=224(MH$^+$)

Description 49

5-Amino-1-(4-pyridylmethyl)indole (D49)

The title compound was prepared by the method of Description 48, from nitroindole D47. Yield 87%.

¹H NMR (CDCl₃) δ: 3.52 (2H, broad), 5.27 (2H, s), 6.41 (1H, d, J=3), 6.63 (1H, dd, J=8,2), 6.90–7.0 (4H, m), 7.05 (1H, d, J=3), 8.50 (2H, d, J=7).
MS(API) m/z=224(MH⁺)

Description 50
5-Nitro-1-(3-pyridyl)indole (D50)

A mixture of 5-nitroindole (0.49 g, 3 mmol), 3-bromopyridine (0.95 g, 6 mmol), copper (I) bromide (60 mg, 0.42 mmol) and potassium carbonate (0.62 g, 4.5 mmol) in pyridine (2 mL) and nitrobenzene (0.6 mL) was heated under reflux for 4 h. After cooling, the mixture was diluted with water and extracted with ethyl acetate. The organic extract was washed with water, dried and evaporated. The residue was chromatographed on silica gel eluted with ethyl acetate to give the tide compound (0.62 g, 86.5%), mp. 164–5° C.
¹H NMR (CDCl₃) δ: 6.93 (1H, d, J=3), 7.49 (1H, d, J=3), 7.51 (1H, d, J=8), 7.57 (1H, dd, J=7,5), 7.87 (1H, dm, J=7), 8.18 (1H, dd, J=8, 2), 8.72 (1H, d, J=5), 8.85 (1H, d, J=2)
MS(API) m/z=240(MH⁺)

Description 51
5-Nitro-1-(4-pyridyl)indole (D51)

The title compound was prepared by the method of Description 50, using 4-bromopyridine. Yield 0.42 g (59%)
¹H NMR (CDCl₃) δ: 7.09 (1H, d, J=3), 7.79 (2H, d, J=6), 7.94 (1H, d, J=8), 8.09 (1H, d, J=3), 8.13 (1H, dd, J=8,2), 8.69 (1H, d, J=2), 8.80 (2H, broad)
MS(API) m/z=240(MH⁺)

Description 52
5-Amino-1-(3-pyridyl)indole (D52)

The title compound was prepared by the method of Description 48, from nitroindole (D50). Crude product was chromatographed on silica gel eluted with ethyl acetate to give the title compound (0.34 g, 63%) as a gum.
¹H NMR (CDCl₃) δ: 3.59 (2H, broad), 6.55 (1H, d, J=3), 6.71 (1H, dd, J=8,2), 6.98 (1H, d, J=2), 7.25 (1H, d, J=3), 7.37 (1H, d, J=8), 7.64 (1H, dd, J=7,5), 7.82 (1H, dm, J=7), 8.58 (1H, d, J=5), 8.81 (1H, d, J=2)
MS(API) m/z=210(MH⁺)

Description 53
5-Amino-1-(4-pyridyl)indole (D53)

A mixture of nitroindole (D51, 0.41 g, 1.8 mmol), tin (II) chloride (1.7 g, 8.8 mmol), and concentrated hydrochloric acid (2 ml) in ethanol (10 ml) was heated under reflux for 70 min. The mixture was evaporated and the residue was dissolved in water, basified with dilute sodium hydroxide and extracted with dichloromethane. The extract was dried and evaporated to give the tide compound (0.36 g, 96%).
¹H NMR (CDCl₃) δ: 3.62 (2H, broad), 6.56 (1H, d, J=3), 6.72 (1H, dd, J=8,2), 6.95 (1H, d, J=2), 7.32 (1H, d, J=3), 7.41 (2H, d, J=6), 7.54 (1H, d, J=8), 8.68 (2H, d, J=6)
MS(API) m/z=210(MH⁺)

Description 54
5-Methylthio-6-trifluoromethyl-1-(3-ethoxycarbonylphenyl carbamoyl)-indoline (D54)

This was prepared in 74% yield by urea formation between ethyl 3-aminobenzoate and 5-methylthio-6-trifluoromethyl indoline, (D7) using carbonyl diimidazole as the coupling agent.

Description 55
5-Methythio-6-trifluoromethyl-1-(3-carboxyphenylcarbamoyl)-indoline (D55)

This was prepared in 86% by basic hydrolysis of the corresponding ester D54.
¹H NMR (CDCl₃) δ: 2.50 (3H, s), 3.30 (2H, t), 4.20 (2H, t), 7.40–7.50 (2H, m), 7.60 (1H, m), 7.85 (1H, d), 8.25 (2H, m), 8.80 (1H, s)

Description 56
4-(3-Nitrophenyl)-2-(3-pyridyl)-thiazole, hydrobromide salt

A mixture of 2-bromo-3'-nitroacetophenone (5 g, 20 mmol) and thionicotinamide (2.76 g, 20 mmol) in ethanol (25 ml) was heated to reflux for 1 h, during which time extensive precipitation occurred. Filtration and drying afforded the product as a yellow solid (6.7 g, 92%).
¹H NMR δ (DMSO) 7.80 (1H, t), 7.95 (1H, m), 8.25 (1H, dd), 8.55 (1H, d), 8.70 (1H, s), 8.90 (3H, m), 9.45 (1H, d)

Description 57
4-(3-Aminophenyl)-2-(3-pyridyl)-thiazole

A suspension of 4-(3-nitrophenyl)-2-(3-pyridyl)-thiazole hydrobromide (3.6 g, 10 mmol) in ethanol (150 ml) was treated with a solution of tin (II) chloride (3.7 g, 30 mmol) in concentrated hydrochloric acid (12 ml). The mixture was heated at 50° C. for 16 h. A further portion of tin (II) chloride (2.9 g, 15 mmol) was added and the mixture heated at 50° C. for a further 4 hours before being evaporated to dryness. The residue was partitioned between ethyl acetate and 1M aqueous sodium hydroxide. The ethyl acetate extract was dried (Na₂SO₄) and filtered through a plug of silica. Evaporation afforded the title compound as a yellow solid (2.15 g, 85%).
¹H NMR (CDCl₃) δ: 3.80 (2H, bs), 6.70 (1H, dd), 7.20 (2H, m), 7.40 (2H, m), 7.50 (1H, s), 8.30 (1H, dt), 8.65 (1H, dd), 9.25 (1H, d).

Description 58
4-(4-Nitrophenyl)-2-(4-pyridyl)-thiazole

This was prepared in the same manner as 4(3-nitrophenyl)-2-(3-pyridyl)-thiazole, hydrobromide salt and liberated to the free base form with 5M NaOH to give the product as a brown solid (4 g, 69%).
¹H NMR (CDCl₃) δ: 8.8 (2H, d), 8.35 (2H, d), 8.15 (2H, d), 7.9 (2H, d), 7.8 (1H, s).

Description 59
4-Fluoro-3-(pyrid-3-yl)phenylcarbonyl azide (D59)

3-Bromo-4-fluorobenzotrifluoride was coupled with 3-pyridylboronic acid using Suzuki methodology. Hydrolysis of the product using conc. sulphuric acid and chlorosulphonic acid followed by esterification in methanol and conc. sulphuric acid gave methyl 4-fluoro-3-(pyrid-3-yl)benzoate. Treatment with hydrazine hydrate afforded the hydrazide which was diazotised with sodium nitrite and basified with potassium carbonate to give the title compound.
¹H NMR 250 MHz δ: 8.82 (br, 1H), 8.67 (br, 1H), 8.17 (dd, 1H), 8.09 (m, 1H), 7.90 (dd, 1H), 7.42 (m, 1H), 7.30 (m, 1H).

Description 60
3-Fluoro-5-(pyrimidin-5-yl)phenylcarbonyl azide (D60)

3-Bromo-5-fluorobenzotrifluoride was lithiated with n-butyllithium and treated with tri-isopropylborate to give 3-fluoro-5-trifluoromethylphenyl boronic acid. This was coupled to 5-bromopyrimidine, using Suzuki methodology to afford 3-fluoro-5-(pyrimidin-5-yl)benzotrifluoride. Hydrolysis with conc. sulphuric acid and chlorosulphonic acid afforded 3-fluoro-5-(pyrimidin-5-yl)benzoic acid. This was converted to the methyl ester by treatment with methanol and conc. sulphuric acid, and to the hydrazide by treatment with hydrazine hydrate. Diazotisation and treatment with potassium carbonate afforded the title compound.
¹H NMR (200 MHz, CDCl₃) δ (ppm): 7.57 (1H, dt J=1, 8), 7.83 (1H, m), 8.06 (1H, t, J=1), 8.99 (2H, s), 9.29 (1H, s)

Description 61
4-Chloro-3-(4-methyl-3-pyridyl)nitrobenzene (D61)

The title compound was prepared by a Suzuki coupling of 3-bromo-4-chloronitrobenzene and 4-methyl-3-pyridylboronic acid. This gave (D61) (0.2 g, 33%).

Description 62
4-Chloro-3-(4-methyl-3-pyridyl)aniline (D62)

The title compound was prepared by stannous chloride reduction of the nitro compound (D61). This gave (D62) (0.105 g, 95%).

Description 63
2,3-Dihydro-5-nitro-7-(pyrid-3-yl)benzofuran (D63)

2,3-Dihydro-7-iodo-5-nitrobenzofuran (0.76 g, 0.0026 mole) and 3-pyridylboronic acid (0.32 g, 0.0026 mole) in 50% aqueous 1,2-dimethoxyethane (50 ml) were treated under argon with sodium carbonate (1.17 g, 0.011 mole) and tetrakis triphenylphosphine palladium (0) (0.06 g, 0.000052 mole) and heated under reflux for 18 hours. The mixture was allowed to cool to ambient temperature, diluted with deionised water, extracted into ethyl acetate, dried ($Na_2SO_4$) and evaporated in vacuo. The residue was purified by flash column chromatography on silica gel, eluting with 30% ethyl acetate/60–80° petroleum ether to afford the title compound (0.19 g, 30%) as a yellow solid.

$^1$H NMR (200 MHz, $CDCl_3$) δ (ppm): 3.40 (2H, t, J=9), 4.83 (2H, t, J=9), 7.40 (1H, q, J=3, 5), 8.02 (1H, dt, J=1,9), 8.12 (1H, m), 8.30 (1H, d, J=3), 8.62 (1H, dd, J=1, 5), 8.98 (1H, d, J=1).

Description 64
5-Amino-2,3-dihydro-7-(pyrid-3-yl)benzofuran (D64)

2,3-Dihydro-5-nitro-7-(pyrid-3-yl)benzofuran (D63) (0.19 g, 0.00079 mole) in ethanol (20 ml) was treated with a solution of tin II chloride (0.75 g, 0.0040 mole) in conc. hydrochloric acid (1 ml) and heated at 50° C. for 2 hours. A further 0.38 g tin II chloride in conc. hydrochloric acid (0.5 ml) was added and the mixture was heated at 50° C. for ½ hour and stirred at ambient temperature for 18 hours. Deionised water (5 ml) was added and the mixture was basified with 10% sodium hydroxide solution, extracted into ethyl acetate, dried ($Na_2SO_4$) and evaporated in vacuo to afford the title compound (0.13 g, 82%) as a dark oil.

$^1$H NMR (200 MHz, $CDCl_3$) δ (ppm): 3.20 (2H, t, J=9), 3.43–3.70 (2H, br s), 4.57 (2H, t, J=9), 6.63 (2H, s), 7.32 (1H, m), 8.01 (1H, dt, J=1, 5), 8.51 (1H, dd, J=1, 5), 8.89 (1H, t, J=1).

Description 65
Phenyl N-[2,3-dihydro-7-(pyrid-3-yl)benzofuran-5-yl] carbamate (D65)

5-Amino-2,3-dihydro-7-(pyrid-3-yl)benzofuran (D64) (0.13 g, 0.00062 mole) was dissolved in dichloromethane (10 ml) and cooled to 0° C. under argon. Triethylamine (0.09 ml, 0.00068 mole) was added, followed dropwise by phenyl chloroformate (0.08 ml, 0.00065 mole) and the mixture was stirred at ambient temperature for 2 hours. The reaction mixture was washed with deionised water, dried ($Na_2SO_4$) and evaporated in vacuo to afford the title compound (0.20 g, 97%) as a cream solid.

$^1$H NMR (200 MHz, $CDCl_3$) δ (ppm): 3.38 (2H, t, J=9), 4.64 (2H, t, J=9), 7.05–7.58 (9H, m), 8.06 (1H, dt, J=1, 5), 8.57 (1H, dd, J=1,5), 8.95 (1H, d, J=1).

Description 66
Phenyl N-(3-Fluoro-5-(pyrid-3-yl)phenyl)carbamate (D66)

3-Fluoro-5-(pyrid-3-yl)aniline (1.05 g, 0.0050 mole) in dry dichloromethane was treated under argon with triethylamine (1.12 ml, 0.0080 mole) followed dropwise by phenyl chloroformate (0.97 ml, 0.0077 mole) and stirred at ambient temperature for 18 hours. The reaction mixture was washed (×2) with deionised water, dried ($Na_2SO_4$) and evaporated in vacuo to afford the title compound (1.1 g, 71%) as an off white solid.

$^1$H NMR (200 MHz; $D^6DMSO$) δ: 7.20–7.49 (3H, m), 7.49–7.59 (5H, m), 7.63 (1H, d), 8.07 (1H, dt), 8.63 (1H, d), 8.87 (1H, s), 10.61 (1H, s)

Description 67
Phenyl N-(4-Chloro-3-(pyrid-3-yl)phenyl)carbamate (D67)

4-Chloro-3-(pyrid-3-yl)aniline (0.08 g, 0.00039 mole) in isopropyl alcohol (8 ml) was cooled to −40° C. and treated under argon with triethylamine (0.06 ml, 0.00043 mole) followed dropwise by phenyl chloroformate (0.051 ml, 0.00041 mole). The reaction mixture was stirred at −40° C. for half an hour and allowed to warm to ambient temperature. The solvent was removed in vacuo and the residue dissolved in dichloromethane, washed with HO, dried ($Na_2SO_4$) and evaporated in vacuo to afford the title compound (0.12 g, 95%) as an orange solid.

$^1$H NMR (200 MHz; $CDCl_3$) δ: 7.05–7.56 (10H, m), 7.82 (1H, dt), 8.64 (1H, dd), 8.71 (1H, d)

Description 68
Phenyl N-[(5-Methyl-1,2,4-oxadiazol-3-yl)phenyl] carbamate (D68)

The title compound (0.23 g, 97%) was prepared using the method of D67.

$^1$H NMR (200 M $CDCl_3$) δ: 2.65 (3H, s), 7.08 (1H, s), 7.16–7.53 (6H, m), 7.66–7.87 (2H, m), 8.06 (1H,t).

Description 69
Phenyl N-[4-Methyl-3-(4-methylpyrid-3-yl)phenyl] carbamate (D69)

The title compound was prepared as in the method of description 67 from the corresponding aniline. This gave (2.1 g, 97%) of an oil.

$^1$H NMR ($CDCl_3$) δ: 2.05 (3H, s), 2.15 (3H, s), 7.08–7.45 (10H, m), 8.30 (1H, s), 8.48 (1H, d, J=8 Hz).

EXAMPLE 1
1-[(3-Pyridyl)-3-phenyl carbamoyl]-5-methoxy-6-trifluoromethyl indoline 3-(3-Pyridyl)aniline (0.27 g, 1.6 mmol) in dichloromethane (5 ml) was added dropwise over 5 minutes to a solution of 1,1-carbonyldiimidazole (0.28 g, 1.75 mmol) in dichloromethane (5 ml). After 2 hour the mixture was evaporated to dryness and the residue dissolved in N,N-dimethylformamide (20 ml). 5-Methoxy-6-trifluoromethyl indoline (0.35 g, 1.6 mmol) was added and the mixture heated to 100° C. for 1 h. Water (30 ml) was added and the mixture was set aside in the fridge for 1 h. Filtration and drying afforded a brown solid (0.59 g). Chromatography on silica, eluting with a gradient of 0–3% methanol in dichloromethane afforded the title compound as a white solid (0.56 g, 85%), mp 193–4° C.

$^1$H NMR ($D^6$ DMSO) 3.25 (2H, t), 3.85 (3H, s), 4.20 (2H, t) 7.20 (1H, s), 7.40 (2H, m), 7.50 (1H, m), 7.90 (1H, s), 8.05 (1H, dm), 8.15 (1H, s), 8.60 (1H, dm), 8.70 (1H, s), 8.85 (1H, s).

The mesylate salt can be prepared by treatment with methanesulphonic acid in acetone.

The following examples were similarly prepared:

EXAMPLE 2
1-[(4-Pyridyl)-3-phenyl carbamoyl]-5-methylthio-6-trifluoromethyl indoline Yield=25%

$^1$H NMR ($D^6$-DMSO) 2.52 (3H, s), 3.30 (2H, t), 4.25 (2H, t), 7.50 (3H, m), 7.70 (3H, m), 8.02 (1H, s), 8.25 (1H, s), 8.70 (2H, dd), 8.80 (1H, s).

EXAMPLE 3
1-[(3-Pyridyl)-3-phenyl carbamoyl]-5-methylthio-6-trifluoromethyl indoline.

Yield=42%, m.p. 208–210° C.

$^1$H MNR ($D^6DMSO$) 2.50 (3H, s), 3.30 (2H, t), 4.20 (2H, t), 7.40 (3H, m), 7.50 (1H, M), 7.65 (1H, m), 7.90 (1H, s), 8.10 (1H, dm), 8.20 (1H, s), 8.60 (1H, m), 8.80 (1H, s), 8.90 (1H, m).

The mesylate salt can be prepared by treatment with methanesulphonic acid in acetone.

EXAMPLE 4

1-[(3-Pyridyl)-4-phenyl carbamoyl]-5-methoxy-6-trifluromethylindoline.

Yield=85%, m.p.=>230° C.

$^1$H NMR (D$^6$-DMSO) 3.30 (2H, t), 3.85 (3H, s), 4.20 (2H, t), 7.20 (1H, s), 7.45 (1H, m), 7.70 (4H, m), 8.05 (1H, m), 8.15 (1H, s), 8.55 (1H, m), 8.70 (1H, s), 8.90 (1H, m)

EXAMPLE 5

1-[(4-Pyridyl)-4-phenyl carbamoyl]-5-methoxy-6-trifluoromethyl indoline

Yield=5%, m.p.=>210° C.

$^1$H NMR (D$^6$-DMSO) 3.30 (2H, t), 3.85 (3H, s), 4.20 (2H, t), 7.20 (1H, s), 7.70 (2H, d), 7.75 (4H, m), 8.15 (1H, s), 8.60 (2H, d), 8.85 (1H, s)

EXAMPLE 6

1-[(2-Pyridyl)-3-phenyl carbamoyl]-5-methoxy-6-trifluoromethyl indoline.

Yield=40%, m.p.=220–225° C.

$^1$H NMR (D$^6$-DMSO) 3.30 (2H, t), 3.85 (3H, s), 4.20 (2H, t), 7.20 (1H, s), 7.40 (2H, m), 7.70 (2H, m), 7.90 (2H, m), 8.15 (1H, s), 8.35 (1H, s), 8.65 (1H, m), 8.70 (1H, s).

EXAMPLE 7

1-[4-Methyl-3-(3-Pyridyl)-phenylcarbamoyl]-5-methoxy-6-trifluoromethyl indoline

Yield=26%, m.p.=211–212° C.

$^1$H NMR (D$^6$-DMSO) 2.2 (3H, s), 3.28 (2H, t), 3.85 (3H, s), 4.11 (2H, t), 6.44 (1H, s), 6.85 (1H, s), 7.18–7.45 (4H, m), 7.59–7.72 (1H, m), 8.22 (1H, s), 8.49–8.69 (2H, m).

The mesylate salt can be prepared by treatment with methanesulphonic acid in acetone.

EXAMPLE 8

1-[3-Fluoro-5-(3-pyridyl)phenylcarbamoyl]-5-methoxy-6-trifluoromethyl indoline.

Yield=26%, m.p.=220–223° C.

$^1$H NMR (D$^6$-DMSO) 3.29 (2H, t), 3.85 (3H, s), 4.21 (2H, t), 7.23 (1H, s), 7.30 (1H, t), 7.54 2H, m), 7.65 (1H, dt), 7.76 (1H, s), 8.09 (1H, dt), 8.15 (1H, s), 8.62 (1H, dd), 8.78–9.00 (2H, m).

The mesylate salt can be prepared by treatment with methanesulphonic acid in acetone. m.p. 198–199° C.

EXAMPLE 9

1-[2-Fluoro-5-(3-pyridyl) phenyl carbamoyl]-5-methoxy-6-trifluoromethyl indoline.

Yield=10%, m.p. 233° C. (decomp)

$^1$H NMR (D$^6$-DMSO) 3.20 (2H, t), 3.82 (3H, s), 3.94 (2H, t), 7.13–7.28 (2H, m), 7.38–7.58 (3H, m), 7.87 (1H, dt), 7.98 (1H, S), 8.35 (1H, S), 8.55 (1H, dd), 8.64 (1H, d)

EXAMPLE 10

1-(5-Phenyl pyrid-3-yl carbamoyl)-5-methoxy-6-trifluoromethyl indoline

A mixture of 1-(5-bromo-pyrid-3-yl carbamoyl)-5-methoxy-6-trifluoromethylindoline (D14, 208 mg, 0.5 mmol), phenyl boronic acid (300 mg, 2.4 mmol), sodium carbonate (0.32 g, 3 mmol) and tetrakis (triphenylphosphine) palladium (0) (30 mg) in dimethoxyethane-water (5 ml-1 ml) was heated to reflux under argon for 10 h. The cooled reaction mixture was partitioned between ethyl acetate-half saturated brine. The organic extract was dried and evaporated affording a brown solid (0.14 g). Chromatography on silica, eluting with a gradient of 0–5% methanol in ethyl acetate afforded the title compound as a white crystalline solid (100 mg, 48%), m.p. 162–164° C.

$^1$H NMR (D$^6$-DMSO) 3.30 (2H, t) 3.85 (3H, s), 4.20 (3H, t), 7.20 (1H, s), 7.50 (3H, m), 7.70 (2H, m), 8.10 1H, s), 8.30 (1H, m), 8.55 (1H, m), 8.75 (1H, m), 8.85 (1H, s).

The mesylate salt can be prepared by treatment with methanesulphonic acid in acetone.

The following examples were similarly prepared:

EXAMPLE 11

1-(5-Phenyl pyrid -3-yl carbamoyl)-5-methylthio-6-trifluoromethyl indoline

Yield=73%, m.p.=208–214° C.

$^1$H NMR (D$^6$-DMSO) 2.50 (2H, s), 3.30 (2H, t), 4.20 (2H, t), 7.50 (4H, m), 7.70 (2H, m), 8.20 (1H, s), 8.30 (1H, m), 8.60 (1H, m), 8.75 (1H, m), 8.95 (1H, s).

EXAMPLE 12

1-[5-(3-Pyridyl)-pyrid-3-yl carbamoyl]-5-methoxy-6-trifluoromethyl indoline.

Yield=29%, m.p.=113–114° C.

$^1$H NMR (D$^6$-DMSO) 3.30 (2H, t), 3.85 (3H, s), 4.20 (2H, t), 7.20 (1H, s), 7.55 (1H, m), 8.10 (1H, m), 8.15 (1H, s), 8.30 (1H, m), 8.60 (1H,), 8.65 (1H, dd), 8.80 (1H, d), 8.95 (2H, m)

The mesylate salt can be prepared by treatment with methanesulphonic acid in acetone.

EXAMPLE 13

1-[5-(4-Trifluoromethylphenyl)-pyrid-3-yl carbamoyl]-5-methoxy-6-trifluoromethyl indoline Yield=48%, m.p.=199–202° C.

$^1$H NMR (D$^6$-DMSO) 3.30 (2H, t), 3.85 (3H, s), 4.20 (2H, t), 7.20 (1H, s), 7.89 (4H, m), 8.10 (1H, s), 8.35 (1H, m), 8.60 (1H, d), 8.80 (1H, d), 8.95 (1H, s).

EXAMPLE 14

1-[5-(4-Methylphenyl)-pyrid-3yl carbamoyl]-5-methoxy-6-trifluoromethyl indoline.

Yield=57%, m.p.=190–191° C.

$^1$H NMR (D$^6$DMSO) 2.35 (3H, s), 3.30 (2H, t), 3.85 (3H s), 4.20 (2H, t), 7.20 (1H, s, 7.30 (2H, d), 7.60 (2H,d), 8.15 (1H, s), 8.25 (1H, m), 8.55 (1H, d), 8.75 (1H, d), 8.85 (1H, s).

EXAMPLE 15

1-[5-(2-Thienyl)-pyrid-3-yl carbamoyl]-5-methoxy-6-trifluoromethyl indoline

Yield=53%, m.p.=193–208° C.

$^1$H NMR (D$^6$-DMSO) 3.30 (2H, t), 3.85 (3H, s), 4.20 (2H, t), 7.20 (2H, m), 7.65 (2H, m), 8.10 (1H, s), 8.25 (1H, t), 8.60 (1H, d), 8.75 (1H, d), 8.90 (1H, s).

The mesylate salt can be prepared by treatment with methanesulphonic acid in acetone.

EXAMPLE 16

1-[5-(3-Thienyl)-pyrid-3-yl carbamoyl]-5-methoxy-6-trifluoromethyl indoline

Yield=30%, m.p.=165–167° C.

$^1$H NMR (D$^6$-DMSO) 3.30 (2H, t), 3.85 (3H, s), 4.20 (2H, t), 7.20 (1H, s), 7.60 (1H, dd), 7.75 (1H, m), 8.0 (1H, m), 8.15 (1H, s, 8.30 (1H, t), 8.65 (1H, d), 8.70 (1H, d), 8.90 (1H, s

EXAMPLE 17
1-[5-(2-Pyrrolyl)-pyrid-3-yl carbamoyl)-5-methoxy-6-trifluoromethyl indoline.

Yield=20%, m.p.=218–219° C.

$^1$H NMR (D$^6$-DMSO) 3.30 (2H, t), 3.85 (3H, s), 4.20 (2H, t), 6.20 (1H, m), 6.55 (1H, m), 6.90 (1H, m), 7.20 (1H, s), 8.15 (2H, m), 8.50 (1H, d), 8.60 (1H, d), 8.80 (1H, s).

EXAMPLE 18
1-[5-(4-Pyridyl)-pyrid-3-yl carbamoyl]-5-methoxy-6-trifluoromethyl indoline Yield=71%, m.pt 230–234° C.

$^1$H NMR (D$^6$-DMSO) 3.30 (2H, t), 3.85 (3H, s), 4.20 (2H, t), 7.20 (1H, s), 7.75 (2H, m) 8.15 (1H, s), 8.40 (1H, t), 8.65 (1H, d), 8.70 (2H, m), 8.85 (1H, d).

EXAMPLE 19
1-[2-(3-Pyridyl)-thiazol-4-yl carbamoyl]-5-methoxy-6-trifluoromethyl indoline.

A solution of acyl azide (D15) (370 mg, 1.6 mmol) in toluene (5 ml) was heated to reflux for 0.25 h. After cooling to room temperature, the solution of the isocyanate was added to a solution of 5-methoxy-6-trifluoromethyl indoline (0.35 g, 1.6 mmol) in dichloromethane (10 ml). Filtration and drying afforded the title compound as a white solid (100 mg, 15%), m.p. >200° C.

$^1$H NMR 3.30 (2H, t), 3.85 (3H, s), 4.20 (2H, t), 7.20 (1H, s), 7.45 (1H, m), 7.55 (1H, s), 8.15 (1H, s, 8.30 (1H, dt), 8.65 (1H, dd), 9.15 (1H, m), 9.85 (1H, s).

EXAMPLE 20
1-[2-(2-Pyridyl)-thien-5-yl carbamoyl]-5-methoxy-6-trifluoromethyl indoline.

This was prepared from the corresponding acyl azide (D16) using the same procedure as for Example 19, affording the title compound as a pale yellow solid (0.45 g, 73%), m.p. 205–215° C.

$^1$H NMR (D$^6$-DMSO) 3.30 (2H, t), 3.85 (3H, s, 4.20 (2H, t), 6.80 (1H, d), 7.15 (1H, m), 7.25 (1H, s),7.50 (1H, d), 7.75 (2H, m), 8.20 (1H, S), 8.45 (1H, m), 9.95 (1H, s).

EXAMPLE 21
1-(3-Fluoro-5-(4-methyl-3-pyridyl)phenylcarbamoyl)-5-methoxy-6-trifluoromethylindoline A mixture of 1-(3-fluoro-5-iodophenylcarbamoyl)-5-methoxy-6-trifluoromethylindoline (D17, 0.31 g, 0.65 mmol), 4-methyl-3-pyridylboronic acid (88 mg, 0.65 mmol), tetrakis (triphenylphosphine) palladium (O) (23 mg, 0.02 mmol) and sodium carbonate (0.31 g, 3.0 mmol) in 1,2-dimethoxyethane (20 mL) and water (2 mL) was heated under reflux for 24 h, then cooled and poured into water. The aqueous mixture was extracted with dichloromethane/methanol, and the organic extract was washed with brine, dried and evaporated. The residue was chromatographed on silica gel eluted with 2–3% methanol/dichloromethane to give the title compound, which was recrystallised from dichloromethane/petrol (80 mg, 28%), Mp 191–5° C.

$^1$H NMR (d$_6$DMSO) δ: 2.31 (3H, s), 3.28 (2H, t, J=8), 3.85 (3H, s), 4.19 (2H, t, J=8), 6.94 (1H, d, J=8), 7.22 (1H, s), 7.37 (1H, d, J=6), 7.42 (1H, s), 7.61 (1H, d, J=12), 8.12 (1H, s), 8.40 (1H, s), 8.46 (1H, d, J=6), 8.82 (1H, s)

MS (API): Found m/z=446 (MH$^+$), $C_{23}H_{19}N_3O_2F_4$ requires M+1=446

EXAMPLE 22
1-(5-(2,6-Difluorophenyl)-3-pyridylcarbamoyl)-5-methoxy-6-trifluoromethylindoline A solution of 5-(2,6-difluorophenyl)nicotinoyl azide (D20, 0.46 g, 1.8 mmol) in toluene (10 mL) was heated under reflux for 2 h. After cooling, a solution of 5-methoxy-6-trifluoromethylindoline (D11, 0.40 g, 1.8 mmol) in dichloromethane (10 mL) was added and the mixture was stirred overnight at room temperature. The precipitate was filtered off and washed with petrol. The crude product was recrystallised from dichloromethane/petrol to give the title compound (0.66 g, 82%), Mp. 217–9° C.

$^1$H NMR (d$_6$DMSO) δ: 3.29 (2H, t, J=8), 3.84 (3H, s), 4.21 (2H, t, J=8), 7.22 (1H, s), 7.29 (2H, t, J=7), 7.56 (1H, quintet, J=7), 8.11 (1H, s), 8.15 (1H, s), 8.32 (1H, s), 8.80 (1H, s), 9.93 (1H, s).

MS (API): m/z=450 (MH$^+$), $C_{22}H_{16}N_3O_2F_5$ requires M+1=450

Found: C, 54.84; H, 3.69; N, 8.64%
$C_{22}H_{16}N_3O_2F_5$ requires C, 58.80: H, 3.59; N, 9.35%

EXAMPLE 23
6-Chloro-5-methyl-1-(4-methyl-3-(pyrid-3-yl)-phenylcarbamoyl) indoline 4-Methyl-3-(pyrid-3-yl) aniline (0.30 g, 0.0016 mole) in dry dichloromethane (20 ml) was added, under argon, to 1,1'-carbonyldiimidazole in dry dichloromethane (10 ml) (0.30 g, 0.0018 mole) and stirred at ambient temperature for 1 hour. The solvent was removed in vacuo and the residue dissolved in dry dimethylformamide (30 ml). 6-Chloro-5-methylindoline (see WO 95/01976) (0.27 g, 0.0016 mole) in dry dimethylformamide (10 ml) was added and the mixture heated to 100° C. for 1 hour. After cooling to ambient temperature, the solvent was removed in vacuo and the residue diluted with deionised water (15 ml), extracted into dichloromethane (2×20 ml), dried (Na$_2$SO$_4$) and evaporated in vacuo. The residue was purified by flash column chromatography on silica gel, eluting with 3% methanol/dichloromethane and the resulting solid recrystallised from ethyl acetate/methanol/60–80° petroleum ether to afford the title compound (0.31 g, 57%) as a cream solid (mp 202–203° C.).

$^1$H NMR (270 MHz, d$^6$DMSO) δ: 2.20 (3H, s), 2.24 (3H, s), 3.12 (2H, t, J=7), 4.13 (2H, t, J=7), 7.14 (1H, s), 7.25 (1H, d, J=7), 7.42–7.61 (3H, m), 7.81 (1H, dt, J=3, 7), 7.89 (1H, s), 8.49–8.69 (3H, m)

MS (EI) m/z=377 (M$^+$)

The mesylate salt can be prepared by treatment with methanesulphonic acid in acetone.

EXAMPLE 24
1-(4-Methyl-3-(pyrid-3-yl) phenylcarbamoyl)-5-thiomethyl-6-trifluoromethyl indoline 4-Methyl-3-(pyrid-3-yl) aniline (0.35 g, 0.0019 mole) in dry dichloromethane (20 ml) was added, under argon, to 1,1'-carbonyldiimidazole (0.34 g, 0.0021 mole) in dry dichloromethane (10 ml) and stirred at ambient temperature for 1 hour. The solvent was removed in vacuo and the residue dissolved in dry dimethylformamide (10 ml). 5-Thiomethyl-6-trifluoromethylindoline (D7) (0.44 g, 0.0019 mole) in dry dimethylformamide (5 ml) was added and the mixture heated to 100° C. for 2 hours. After cooling to ambient temperature, the solvent was removed in vacuo and the residue diluted with deionised water (15 ml), extracted into dichloromethane (2×20 ml), dried (Na$_2$SO$_4$) and evaporated in vacuo. The residue purified by flash column chromatography on silica gel eluting with 3% methanol/dichloromethane and the resulting solid was recrystallised from ethyl acetate/60–80° petroleum ether to afford the title compound (0.11 g, 13%) as a cream solid (mp 221–223° C.)

$^1$H NMR (200 MHz; d$^6$DMSO) δ: 2.20 (3H, s), 2.55 (3H, s), 3.38 (2H, t, J=8), 4.20 (2H, t, J=8), 7.26 (1H, d, J=9), 7.41–7.61 (4H, m), 7.81 (1H, dt, J=3,9), 8.20 (1H, s), 8.51–8.63 (2H, m), 8.69 (1H, s)

MS (CI) m/z=444 (MH$^+$)

EXAMPLE 25

1-(3-Fluoro-5-(pyrid-3-yl)phenylcarbamoyl)-5-thiomethyl-6-trifluoromethyl-indoline hydrochloride Phenyl N-(3-fluoro-5-(pyrid-3-yl)phenyl)carbamate (D66) (0.55 g, 0.0018 mole) in dry dimethylformamide (30 ml) was treated, under argon, with 5-thiomethyl-6-trifluoromethyl indoline hydrochloride (D7) (0.49 g, 0.0018 mole) and triethylamine (0.5 ml, 0.0036 mole) and heated to 100° C. for 6 hours. After cooling to ambient temperature, the solvent was removed in vacuo. The residue was purified by flash column chromatography on silica gel, eluting with 3% methanol/dichloromethane and the resulting solid recrystallised from ethyl acetate/60–80° petroleum ether to afford the title compound (0.39 g, 49%) as an off white solid (mp 202–203° C.)

$^1$H NMR (250 MHz, d$^6$DMSO) δ: 2.52 (3H, s), 3.32 (2H, t, J=8), 4.22 (2H, t, J=8), 7.30 (1H, d, J=8), 7.45–7.58 (3H, m), 7.64 (1H, d, J=11), 7.78 (1H, s), 8.09 (1H, d, J=8), 8.23 (1H, s), 8.63 (1H, d, J=6), 8.87–9.01 (2H, m)

MS (Electron Spray) m/z=448 (MH$^+$)

EXAMPLE 26

1-(4-Chloro-3-(pyrid-3-yl)phenylcarbamoyl)-5-methoxy-6-trifluoromethylindoline

Phenyl N-(4-Chloro-3-(pyrid-3-yl)phenyl)carbamate (D67) (0.12 g, 0.00037 mole) in dry dimethylformamide (6 ml) was treated under argon, with 5-methoxy-6-trifluoromethylindoline (D11) (0.08 g, 0.00037 mole) and heated to 120° C. for 2 hours. After cooling to ambient temperature, the solvent was removed in vacuo. The residue was partitioned between 1N aqueous sodium hydroxide solution and dichloromethane. The organic layer was dried (Na$_2$SO$_4$) and evaporated in vacuo. The residue was triturated in diethyl ether, filtered and dried in vacuo at 60° C. to afford the title compound (0.06 g, 36%) as a grey-green solid (mp 210–213° C.)

$^1$H NMR (200 MHz; CDCl$_3$) δ: 3.30 (2H, t, J=9), 3.87 (3H, s), 4.12 (2H, t, J=9), 6.56 (1H, s), 6.87 (1H, s), 7.29–7.58 (4H, m), 7.81 (1H, d, J=8), 8.21 (1H, s), 8.60 (1H, d, J=5), 8.69 (1H, d, J=3).

MS (EI) m/z=447 (M$^+$)

EXAMPLE 27

5-Methoxy-1-(5-methyl-(1,2-4-oxadiazol-3-yl)-phenylcarbamoyl)-6-trifluoromethyl indoline (E27)

Phenyl N-(5-Methyl-(1,2,4-oxadiazol-3-yl)phenyl) carbamate (D68) (0.23 g, 0.00078 mole) in dry dimethylformamide (10 ml) was treated, under argon, with 5-methoxy-6-trifluoromethylindoline (0.17 g, 0.00078 mole) (D11) and heated to 120° C. for 4 hours. After cooling to ambient temperature, the solvent was removed in vacuo. The residue was partitioned between water and dichloromethane and the organic layer was dried (Na$_2$SO$_4$) and evaporated in vacuo. The residue was purified by flash column chromatography on silica gel eluting with 5% methanol/dichloromethane. The resulting solid was recrystallised from ethyl acetate/60–80° petroleum ether to leave the title compound (0.11 g, 34%) as a beige solid (mp 203–204° C.)

$^1$H NMR (250 MHz; d$^6$DMSO) δ: 2.68 (3H, s), 3.30 (2H, t, J=8), 3.85 (3H, s), 4.21 (2H, t, J=8), 7.21 (1H, s), 7.49 (1H, t, J=7), 7.66 (1H, d, J=7), 7.81 (1H, d, J=7), 8.16 (1H, s), 8.33 (1H, s), 8.82 (1H, s)

MS (Electron Spray) m/z=419 (MH$^+$)

EXAMPLE 28

1-[4-Methyl-3-(4-methyl-3-pyridyl)phenylcarbamoyl]-5-methoxy-6-trifluoromethyl indoline (E28)

Phenyl N-(4-Methyl-3-(4-methylpyrid-3-yl)phenyl) carbamate (D69) (0.5 g, 0.0016 mole) in dry dimethylformamide (20 ml) was treated with 5-methoxy-6-trifluoromethylindoline (D11) (0.34 g, 0.0016 mole) under argon and heated to 100° C. for 6 hrs. The mixture was allowed to cool and evaporated to dryness in vacuo. The residue was dissolved in dichloromethane and the solution washed with 10% aqueous sodium hydroxide solution (2×20 ml) and then with saturated aqueous sodium chloride solution (30 ml). The organic phase was then dried (Na$_2$SO$_4$) filtered and evaporated to dryness. The residue was purified by flash chromatography on silica gel eluting with 1% methanol/dichloromethane. Trituration of the resulting residue with diethyl ether gave the title compound (E28) (0.326 g, 47%) m.p. 138–140° C.

$^1$H NMR (CDCl$_3$) δ: 2.00 (3H, s), 2.13 (3H, s), 3.25 (2H, t, J=8 Hz), 3.82 (3H, s), 4.12 (2H, t, J=8 Hz), 6.62 (1H, s), 6.81 (1H, s), 7.11–7.29 (3H, m), 7.39–7.45 (1H, m), 8.20 (1H, s), 8.30 (1H, s), 8.44 (1H, d, J=6 Hz)

M.S. found 442 (MH$^+$), C$_{24}$H$_{22}$N$_3$O$_2$F$_3$H$^+$ requires 442

EXAMPLE 29

1-[5-Bromo-3-(pyrid-3-yl)phenylcarbamoyl]-5-methoxy-6-trifluoromethylindoline (E29)

The title compound was prepared from phenyl N-[3-bromo-5-(pyrid-3-yl)phenyl]carbamate (D21) and 5-methoxy-6-trifluoromethylindoline (D11) using the method of Example 28.

$^1$H NMR 250 MHz CDCl$_3$ δ: 8.74 (1H, s, Ar), 8.54 (dd, 1H, Ar), 8.19 (s, 1H, Ar), 7.88 (d, 1H, Ar), 7.74 (s, 1H, Ar), 7.6 (s, 1H, Ar), 7.32–7.44 (m, 2H, Ar), 6.82 (br s, 1H, Ar), 4.15 (t, 2H, indoline), 3.85 (s, 3H, Me), 3.25 (t, 2H, indoline)

EXAMPLE 30

1-[4-t-Butyl-3-(pyrid-3-yl)phenylcarbamoyl]-5-methoxy-6-trifluoromethylindoline (E30)

The title compound (0.055 g, 23%) was prepared from phenyl N-[4-t-butyl-3-(pyrid-3-yl)phenyl]carbamate (D22) (0.18 g, 0.00052 mole) and 5-methoxy-6-trifluoromethylindoline (D11) using the method of Example 28.

$^1$H NMR (200 MHz, CDCl$_3$) δ: 1.25 (9H,s), 3.27 (2H, t, J=11), 3.85 (3H, s), 4.09 (2H, t, J=11), 6.43 (1H, s), 6.85 (1H, s), 7.00 (1H, d, J=1), 7.18–7.35 (1H, m), 7.39–7.69 (3H, m), 8.20 (1H, s), 8.42–8.69 (2H, m)

MS (Electron Spray) m/z=470 (MH$^+$)

EXAMPLE 31

1-[4-Methoxy-3-(pyrid-3-yl)phenylcarbamoyl]-5-methoxy-6-trifluoromethylindoline (E31)

The title compound (0.21 g, 32%) was prepared from phenyl N-[4-methoxy-3-(pyrid-3-yl)phenyl]carbamate (D23) (0.48 g, 0.0015 mole) and 5-methoxy-6-trifluoromethylindoline (D11) using the method of Example 28.

$^1$H NMR (200 MHz, D$^6$DMSO) δ: 3.26 (2H, t, J=9), 3.76 (3H, s), 3.83 (3H, s), 4.14 (2H, t, J=9), 7.10 (1H, d, J=7), 7.19 (1H, s), 7.45 (1H, dd, J=1,5), 7.54 (1H, s), 7.59 (1H, d, J=3), 7.87 (1H, dt, J=1,5), 8.10 (1H, s), 8.47–8.55 (2H, m), 8.67 (1H, d, J=3).

MS (Electron Spray) m/z=444 (MH$^+$)

The mesylate salt can be prepared by treatment with methanesulphonic acid in acetone.

EXAMPLE 32
1-[5-Fluoro-4-methoxy-3-(pyrid-3-yl)phenylcarbamoyl]-5-methoxy-6-trifluoromethylindoline (E32)

The title compound (0.34 g, 53%) was prepared from phenyl N-[5-fluoro-4-methoxy-3-(pyrid-3-yl)phenyl) carbamate (D24) (0.48 g, 0.0014 mole) and 5-methoxy-6-trifluoromethylindoline (D11) using the method of Example 28.

$^1$H NMR (200 MHz, D$^6$DMSO) δ: 3.38 (2H, t, J=8), 3.68 (3H, s), 3.84 (3H, s), 4.17 (2H, t, J=8), 7.21 (1H, s), 7.43 (1H, s), 7.51 (1H, dd, J=5, 9), 7.66 (1H, dd, J=3, 20), 7.91 (1H, dt, J=1,8), 8.12 (1H, s), 8.61 (1H, dd, J=3,5), 8.70 (1H, d, J=3), 8.75 (1H, s).

MS (Electron Spray) m/z=462 (MH$^+$)

EXAMPLE 33
1-[3-Bromo-4-methyl-5-(3-pyridyl)phenylcarbamoyl]-5-methoxy-6-trifluoromethylindoline (E33)

A mixture of 1-(3,5-dibromo-4methylphenylcarbamoyl)-5-methoxy-6-trifluoromethylindoline (D25, 0.51 g, 1 mmol), 3-pyridylboronic acid (0.12 g, 1 mmol), tetrakis(triphenylphosphine)palladium (0) (35 mg, 0.03 mmol) and sodium carbonate (0.41 g, 4 mmol) in dimethoxyethane (30 mL) and water (3 mL) was heated under reflux, under argon, for 18 h. The mixture was cooled and poured into water. The precipitate was filtered off, washed with water and dried. The crude product was chromatographed on silica gel, eluted with ethyl acetate, and the eluted material was triturated with ether to give the title compound (0.14 g, 28%), m.p. 216–8° C.

NMR (d$_6$-DMSO) δ: 2.20 (3H, s), 3.25 (2H, t, J=8), 3.84 (3H, s), 4.15 (2H, t, J=8), 7.20 (1H, s), 7.50 (1H, s+1H, m), 7.82 (1H, d, J=7), 8.03 (1H, s), 8.11 (1H, s), 8.57 (1H, s), 8.62 (1H, d, J=4), 8.71 (1H, s).

MS (API) m/z 506 (MH$^+$, $^{79}$Br), 508 (MH$^+$, $^{81}$Br)

EXAMPLE 34
1-[3-(4-Isoquinolyl)phenylcarbamoyl]-5-methoxy-6-trifluoromethyl indoline The title compound was prepared by the method of Example 23, from 4-(3-aminophenyl)isoquinoline (0.41 g, 1.9 mmol), 1,1'-carbonyldiimidazole (0.33 g, 2 mmol) and 5-methoxy-6-trifluoromethylindoline (D11) (0.41 g, 1.9 mmol). Crude product was chromatographed on silica gel eluted with 5% methanol/dichloromethane and eluted material was recrystallised from dichoromethane to give the title compound (0.22 g, 25%), m.p. 211–5° C.

NMR (d$_6$-DMSO) δ: 3.28 (2H, t, J=8), 3.85 (3H, s), 4.21 (2H, t, J=8), 7.20 (1H, d, J=7), 7.22 (1H, s), 7.50 (1H, t, J=8), 7.76 (2H, m), 7.78 (1H, s), 7.82 (1H, t, J=7), 7.93 (1 h, d, J=8), 8.1 (1H, s), 8.25 (1H, d, J=8), 8.47 (1H, s), 8.73 (1H, s), 9.38 (1H, s)

Found: C, 67.01; H, 4.51; N, 9.03%
$C_{26}H_{20}N_3O_2F_3$ requires C, 67.38; H, 4.35; N, 9.07%
MS (API) 464 (MH$^+$)

The mesylate salt can be prepared by treatment with methanesulphonic acid in acetone.

EXAMPLE 35
1-[5-(4-Methyl-3-pyridyl)-pyrid-3-ylcarbamoyl]-5-methoxy-6-trifluoromethylindoline (E35)

1-[5-Bromo-(3-pyridylcarbamoyl]-5-methoxy-6-trifluoromethylindoline (D26) (0.3 g, 0.7 mmoles) and 4-methyl-3-pyridylboronic acid (0.12 g, 0.9 mmoles) was heated under reflux in dimethoxyethane (80 ml) and water (10 ml) with sodium carbonate (0.15 g, 1.4 mmoles) and palladium tetrakis triphenylphosphine (0.1 g, 12 mole %) under an inert atmosphere for 18 hours. After cooling the mixture was partitioned between ethyl acetate (250 ml) and water (200 ml). The organic layer was separated and washed with saturated sodium chloride solution then dried (Na$_2$SO$_4$). Evaporation of the solvent followed by flash chromatography on silica gel eluting with 3–7% MeOH/CH$_2$Cl$_2$ and recrytallisation from ethyl acetate/60–80 petrol gave the title compound (E35) (0.2 g, 65%) m.p. 125–8° C.

$^1$H NMR (CDCl$_3$) δ: 2.32 (3H, s), 3.32 (2H, t, J=8 Hz), 3.85 (3H, s), 4.18 (2H, t, J=8 Hz), 6.90 (2H, s), 7.21 (1H, d, J=4 Hz), 8.10 (1H, s), 8.18 (1H, s), 8.27 (1H, s), 8.40 (1H, s), 8.45–8.53 (2H, m).

M.S. found m/z 429 (MH$^+$) $C_{22}H_{19}N_4O_2F_3$ requires 429.

EXAMPLE 36
1-[6-(3-Pyridyl)-pyrid-3-ylcarbamoyl]-5-methoxy-6-trifluoromethylindoline Reaction of Phenyl N-[6-(pyrid-3-yl)pyrid-3-yl] carbamate (D27) (0.66 g, 2.3 mmoles) with 5-methoxy-6-trifluoromethylindoline (D11) (0.5 g, 2.3 mmoles) as in the method of example 28 gave the title compound (E36) (0.73 g, 78%) m.p. >270° C.

$^1$H NMR (DMSO-d$^6$) δ: 3.32 (2H, t, J=8 Hz), 3.88 (3H, s), 4.23 (2H, t, J=8 Hz), 7.20 (1H, s), 7.45–7.55 (1H, m), 7.98–8.18 (3H, m), 8.35–8.43 (1H, m), 8.55–8.60 (1H, m), 8.85 (1H, d, J=4 Hz), 8.91 (1H, s), 9.23 (1H, s).

MS (API) found m/z 415 (MH$^+$) $C_{21}H_{17}N_4O_2F_3$ requires 415

EXAMPLE 37
1-[5-(2-Furyl)-pyrid-3-ylcarbamoyl-5-methoxy-6-trifluoromethyl indoline (E37)

This was prepared from 1-(5-bromopyrid-3-ylcarbamoyl)-5-methoxy-6-trifluoromethyl indoline and 2-furylboronic acid by the same method as for Example 10, affording the title compound as a pale brown crystalline solid in 80% yield, m.p. 92–94° C.

$^1$H NMR (D$^6$-DMSO) 3.30 (2H, t), 3.85 (3H, s), 4.20 (2H, t), 6.65 (1H, m), 7.10 (1H, d), 7.25 (1H, s), 7.85 (1H, s), 8.15 (1H, s), 8.30 (1H, t), 8.60 (1H, d), 8.65 (1H, d), 8.90 (1H, bs).

EXAMPLE 38
1-[2-(4-Pyridyl)-thiazol-4-ylcarbamoyl-5-methoxy-6-trifluoromethyl indoline This was prepared from 2-(4-pyridyl)-thiazole-4-carboxylic acid by the same methodology as for Description 15 and Example 19, affording the title compound as a yellow crystalline solid in 8% overall yield, m.p. >220° C.

$^1$H NMR (D$^6$-DMSO) 3.30 (2H, t), 3.85 (3H, s), 4.20 (2H, t), 7.20 (1H, s), 7.75 (1H, s), 7.90 (2H, d), 8.15 (1H, s), 8.70 (2H, d), 9.90 (1H, bs).

EXAMPLE 39
1-[2-(Pyrazinyl)-thiazol-4-ylcarbamoyl]-5-methoxy-6-trifluoromethyl-indoline This was prepared from 2-pyrazinyl-thiazole-4-carboxylic acid by the same methodology as for Description 15 and Example 19, affording the title compound as a yellow crystalline solid in 45% overall yield, m.p. >240° C.

$^1$H NMR (D$^6$-DMSO) 3.30 (2H, t), 3.85 (3H, s), 4.20 (2H, t), 7.20 (1H, s), 7.75 (1H, s), 8.20 (1H, s), 8.75 (2H, m), 9.30 (1H, s), 9.90 (1H, s)

EXAMPLE 40
1-[3-(5-Pyrimidyl)phenylcarbamoyl]-5-methoxy-6-trifluoromethyl-indoline This was prepared from 3-(5-pyrimidyl)-aniline (D29) and 5-methoxy-6-trifluoromethyl-indoline (D11), according to the method of Example 1, affording the title compound in 69% yield as a white crystalline solid, m.p. 226–8° C.

$^1$H NMR (D$^6$-DMSO) 3.30 (2H, t), 3.85 (3H, s), 4.20 (2H, t), 7.20 (1H, s), 7.45 (2H, m), 7.70 (1H, m), 7.95 (1H, s), 8.15 (1H, s), 8.70 (1H, s), 9.10 (2H, s), 9.20 (1H, s)

EXAMPLE 41

1-[3-(4-Methyl-3-pyridyl)phenylcarbamoyl]-5-methoxy-6-trifluoromethylindoline

Reaction of phenyl-N-[3-(4-methylpyrid-3-yl)phenyl] carbamate (D28) (0.4 g, 1.3 mmoles) with 5-methoxy-6-trifluoromethylindoline (D11) (0.28 g, 1.3 mmoles) as in the method of Example 28 gave the title compound (E41) (0.19 g, 34%) m.p. 178–180° C.

$^1$H NMR (DMSO-d$^6$) δ: 2.29 (3H, s), 3.29 (2H, t, J=8 Hz), 3.84 (3H, s), 4.19 (2H, t, J=8 Hz), 7.01 (1H, d, J=6 Hz), 7.20 (1H, s), 7.31–7.43 (2H, m), 7.55–7.62 (2H, m), 8.10 (1H, s), 8.32 (1H, s), 8.40 (1H, d, J=6 Hz), 8.62 (1H, s).

M.S. (API) found m/z 428 (MH$^+$) C$_{23}$H$_{20}$N$_3$O$_2$F$_3$ requires 428

EXAMPLE 42

1-[5-Ethyl-3-(pyrid-3-yl)phenylcarbamoyl]-5-methoxy-6-trifluoromethylindoline

The title compound (0.15 g, 40%) was prepared as a tan powder using the methodology of Example 28 from phenyl N-(3-ethyl-5-(pyrid-3-yl)phenyl carbamate (D30) (0.26 g, 0.81 mmol) and 5-methoxy-6-trifluoromethyl indoline (D11) (0.177 g, 0.81 mmol) in DMF (10 ml). Melting point: 205° C.–207° C.

$^1$H NMR 250 MHz, CDCl$_3$ δ: 8.81 (s, 1H, Ar), 8.58 (d, 1H, Ar), 8.22 (s, 1H, Ar), 7.88 (m, 1H, Ar), 7.48 (s, 1H, Ar), 7.32 (m, 2H, Ar), 7.12 (s, 1H, Ar), 6.85 (s, 1H, Ar), 6.52 (s, 1H, NH), 4.12 (t, 2H, indoline), 3.88 (s, 3H, Me), 3.28 (t, 2H, indoline), 2.60 (q, 2H, CH$_2$), 1.3 (t, 3H, Me).

Mass spec. m/z=442 [M$^+$1]$^+$

EXAMPLE 43

5-Methoxy-1-[5-phenyl-3-(pyrid-3-yl)phenylcarbamoyl]-6-trifluoromethyl indoline (E43)

The title compound (0.74 g, 47%) was prepared as an off white solid using the methodology of example 28, with phenyl N-(5-phenyl-3-(pyrid-3-yl)phenyl)carbamate (D31) (0.27 g, 0.76 mmol) and 5-methoxy-6-trifluoromethyl indoline (D11) [0.182 mg, 0.83 mmol) in DMF (10 ml). Melting point: 150°–151° C.

$^1$H NMR 250 MHz CDCl$_3$ δ: 8.87 (s, 1H, Ar), 8.60 (d, 1H, Ar), 8.24 (s, 1H, Ar), 7.90 (m, 1H, Ar), 7.70–7.55 (m, 4H, Ar), 7.50–7.30 (m, 5H, Ar), 6.85 (br, 1H, Ar), 6.65 (br, 1H, NH), 4.12 (t, 2H, indoline), 3.85 (3H, s, Me), 3.28 (t, 2H, indoline)

EXAMPLE 44

6-Chloro-5-methyl-1-[4-methyl-3-(4-methyl-3-pyridyl) phenyl carbamoyl]indoline

Reaction of phenyl N-[4-methyl-3-(4-methylpyrid-3-ylphenyl)carbamate (D69) (0.5 g, 1.6 mmoles) with 6-chloro-5-methylindoline (see WO 95/01976) (0.26 g, 1.6 mmoles) as in the method of Example 28 gave the title compound (E44) (0.23 g, 38%) m.p. 178–180° C.

$^1$H NMR (CDCl$_3$) δ: 2.01 (3H, s), 2.12 (3H, s), 2.29 (3H, s), 3.15 (2H, t, J=8 Hz), 4.07 (2H, t, J=8 Hz), 6.60 (1H, s), 6.95 (1H, s), 7.15–7.28 (3H, m), 7.38–7.43 (1H, m), 7.95 (1H, s), 8.30 (1H, s), 8.42 (1H, s)

MS (API) found m/z 392 (MH$^+$, $^{35}$Cl), 394 (MH$^+$, $^{37}$Cl) C$_{23}$H$_{22}$N$_3$OCl requires 392, 394

EXAMPLE 45

1-[3-(pyrid-3-ylaminocarbonyl)-phenylcarbamoyl]-5-methoxy-6-trifluoromethyl-indoline A mixture of 3-(3-aminobenzoylamino)pyridine (D33) (0.416 g, 2 mmol) and carbonyl diimidazole (0.34 g, 2 mmol) in dichloromethane/N,N-dimethylformamide (25 ml/0.25 ml) was heated to reflux for 0.25 h, then evaporated to dryness. The residue was dissolved in N,N-dimethylformamide (15 ml) and 5-methoxy-6-trifluoromethyl indoline (0.416 g, 2 mmol) was added. The mixture was heated to 100° C. for 1 h then treated with water (30 ml). Filtration and drying afforded a white solid (0.5 g). Chromatography on silica eluting with a gradient of 0–20% methanol in ethyl acetate afforded the title compound as a white solid (0.17 g, 19%), m.p. >220° C.

$^1$H NMR (D6-DMSO) 3.25 (2H, t, J 8 Hz), 3.85 (3H, s), 4.20 (2H, t, J 8 Hz), 7.25 (1H, s), 7.40–7.55 (2H, m), 7.65 (2H, d, J 8 Hz), 7.90 (1H, d, J 8 Hz), 8.10–8.30 (3H, m), 8.40 (1H, d, J 2 Hz), 8.10–8.30 (3H, m), 8.40 (1H, d, J 2 Hz), 8.85 (1H, s), 8.90 (1H, d, J 2 Hz), 10.50 (1H, s).

m/e 457 [MH]$^⊕$ C$_{23}$H$_{19}$N$_4$F$_3$O$_3$ requires 457

EXAMPLE 46

1-[3-(Pyrid-3-ylaminocarbonyl)-phenylcarbamoyl]-5-methylthio-6-trifluoromethyl-indoline To a suspension of 5-methylthio-6-trifluoromethyl-1-(3-carboxy phenyl carbamoyl)indoline (D36) (0.5 g, 1.25 mmol) in dichloromethane was added oxalyl chloride (0.324 g, 2.5 mmol) and dimethylformamide (3 drops). After effervescence had subsided the reaction mixture was evaporated under reduced pressure before being dissolved in tetrahydrofuran (10 ml) and added dropwise to a solution of 3-aminopyridine (0.133 mg, 1.4 mmol) and triethylamine (0.141 g, 1.4 mmol) in tetrahydrofuran (10 ml) at 0° C.

After 1 hour water was added forming a white precipitate which was filtered and dried to yield the product as a white solid (0.435 g, 73%), mp 195–7° C.

$^1$H NMR (DMSO) δ: 10.5 (1H, s); 9.0 (2H, d, J5 Hz); 8.4 (1H, d, J5 Hz); 8. (1H, s); 8.25 (1H, s); 8.2 (1H, s); 7.9 (1H, d, J7 Hz); 7.7 (1H, d, J7 Hz); 7.5 (3H, m); 4.3 (2H, t, J8 Hz); 3.3 (2H, t, J8 Hz); 2.5 (3H, s)

EXAMPLE 47

1-[3-(Pyrid-4-ylaminocarbonyl)-phenylcarbamoyl]-5-methylthio-6-trifluoromethyl indoline This was made in the same manner as Example 46 using a solution of 4-aminopyridine to give the product as a peach solid (0.45 g, 76%), mp >200° C.

$^1$H NMR (DMSO) δ: 10.7 (1H, s); 8.95 (1H, s); 8.5 (2H, d, J7 Hz); 8.2 (1H, s); 8.1 (1H, s); 7.85 (1H, d, J7 Hz); 7.8 (2H, d, J7 Hz); 7.65 (1H, d, J7 Hz); 7.45 (2H, m); 4.25 (2H, t, J7 Hz); 3.3 (2H, t, J7 Hz); 2.5 (3H, s)

m/e=472 C$_{23}$H$_{19}$F$_3$N$_4$O$_2$S requires 472

EXAMPLE 48

1-[4-(Pyrid-3-ylaminocarbonyl)-phenylcarbamoyl]-5-methylthio-6-trifluoromethyl indoline This was made in the same manner as Example 46 using 5-methylthio-6-trifluoromethyl-1-(4-carboxy phenyl carbamoyl) indoline (D37) to give the product as a pale yellow solid (0.327 g, 55%), mp >200 ° C.

$^1$H NMR (DMSO) δ: 10.6 (1H, s); 9.1 (1H, s); 9.0 (1H, s); 8.4 (2H, d, J7 Hz); 8.2 (1H, s); 8.0 (2H, d, J7 Hz); 7.8 (2H, d, J7 Hz); 7.6 (1H, q, J5 Hz); 7.4 (1H, s); 4.25 (2H t, J7 Hz); 3.3 (2H, t, J7 Hz); 2.5 (3H, s).

m/e=472 C$_{23}$H$_{19}$F$_3$N$_4$O$_2$S requires 472

EXAMPLE 49

1-[4-(Pyrid-4-ylaminocarbonyl)-phenylcarbamoyl]-5-methylthio-6-trifluoromethyl indoline This was made in the same manner as Example 48 using a solution of 4-aminopyridine to give the product as an orange solid (0.352 g, 59%), mp 158–160° C.

¹H NMR (DMSO) δ: 10.5 (1H, s); 8.95 (1H, s); 8.5 (2H, d, J5 Hz); 8.2 (1H, s); 7.9 (2H, d, J7 Hz); 7.85 (2H, d, J5 Hz); 7.8 (2H, d, J7z); 7.5 (1H, s); 4.25 (2H, t, J7 Hz); 3.3 (2H, t, J7 Hz); 2.5 (3H, s).

m/e=472 C₂₃H₁₉F₃N₄O₂5 requires 472

EXAMPLE 50

1-[3-(3-pyridylcarbonyl)phenylcarbamoyl]-5-methoxy-6-trifluoromethyl indoline

The title compound (0.17 g, 26%) was prepared using the method of Example 45, and purified by flash column chromatography on silica gel, eluting with 2% methanol/dichloromethane, and recyrstallisation from ethylacetate/methanol/60–80° petroleum ether.

¹H NMR (200 MHz; D⁶DMSO) δ: 3.28 (2H, t), 3.75 (3H, s), 4.20 (2H, t), 7.22 (1H, s), 7.38–7.49 (1H, m), 7.52 (1H, t), 7.63 (1H, q), 7.93–8.00 (1H, m), 8.02 (1H, d), 8.08–8.20 (2H, m), 8.78–8.99 (2H, m), 9.02 (1H, d)

EXAMPLE 51

1-[3-(Pyrid-3-yl-aminosulphonyl)-phenylcarbamoyl]5-methoxy-6-trifluoromethyl-indoline A suspension of 3-(pyrid-3-ylaminosulphonyl)-aminobenzene (D39) (0.5 g, 2 mmol) in chloroform (40 ml) was treated with triethylamine (5 ml) and chlorotrimethylsilane (5 ml). The solution was evaporated to dryness, and the residue dissolved in dichloromethane (20 ml). Carbonyl diimidazole (0.32 g, 2 mmol) was added and after 1 h the reaction mixture was evaporated to dryness. Dimethylformamide (20 ml) and 5-methoxy-6-trifluoromethyl indoline (0.43 g, 2 mmol) was added, and the mixture heated to 100° C. for 2 h. The cooled solution was diluted with water (60 ml). Filtration and drying afforded a brown solid (0.6 g). Chromatography, eluting with 0–5% methanol in ethyl acetate afforded the product as a white solid (0.26 g, 26%), m.p. >215° C.

¹H NMR (DMSO) δ: 10.60 (1H, s), 8.9 (1H, s), 8.30 (1H, d, J2 Hz), 8.25 (1H, dd, J5 Hz, 2 Hz), 8.20 (1H, t, J2 Hz), 8.10 (1H, s), 7.80 (1H, d, J7 Hz), 7.35–7.55 (3H, m), 7.30 (1H, m), 7.20 (1H, s), 4.20 (2H, t, J8 Hz), 3.85 (3H, s), 3.25 (2H, t, J8 Hz)

EXAMPLE 52

5-Methylthio-6-trifluoromethyl-1-[6-(pyridin-3-yloxy)pyridin-3-ylcarbamoyl)]indoline 5-Amino-2-(pyridin-3-yloxy)pyridine (0.5 g, 2.7 mmol) in dichloromethane (25 ml) was treated with triethylamine (0.4 ml, 2.9 mmol) then phenyl chloroformate (0.34 ml, 2.7 mmol) dropwise at −20° C. The reaction mixture was allowed to warm to room temperature over 1 hour then poured into dilute aqueous sodium bicarbonate (50 ml). The organic phase was separated and the aqueous phase extracted with dichloromethane (2×50 ml). The combined organic phases were dried (Na₂SO₄) and evaporated to give the crude phenyl carbamate (0.84 g) as a crystallising oil. This material was taken-up in dry DMF (10 ml) and triethylamine (0.5 ml) and treated with 5-methylthio-6-trifluoromethyl indoline hydrochloride (0.63 g, 2.32 mmol) at 100° C. for 0.5 h. After cooling the DMF was removed under reduced pressure and the residue was partitioned between 5% aqueous sodium hydroxide (100 ml) and dichloromethane (3×100 ml). The combined organic extracts were dried (Na₂SO₄) and evaporated. Chromatography using 2% methanol in ethyl acetate as eluant followed by recrystallisation from ethyl acetate/petroleum ether (60–80°) gave the title compound (0.88 g, 73%) as a white crystalline solid m.p. 193–4° C.

¹H NMR (250 MHz, DMSO) δ: 3.28 (2H, t, J 8 Hz), 3.37 (3H, s), 4.20 (2H, t, J 8 Hz), 7.13 (1H, d, J 9 Hz), 7.42–7.51 (2H, m), 7.61 (1H, m), 8.08 (1H, dd, J 8 Hz, 2 Hz), 8.21 (1H, s), 8.27 (1H, d, J 2 Hz), 8.40–8.48 (2H, m), 8.86 (1H, s).

MS (EI) m/e=447 (MH⁺)

EXAMPLE 53

5-Methoxy-6-trifluoromethyl-1-[6-(pyridin-3-yloxy)pyridin-3-ylcarbamoyl]indoline 5-Amino-2-(pyridin-3-yloxy)pyridine (0.2 g, 1.1 mmol) was treated with phenyl chloroformate to give the phenyl carbamate which was treated with 5-methoxy-6-trifluoromethylindoline (0.23 g, 1.1 mmol) according to the method of Example 52 to give the title compound (0.34 g , 74%) as a whiter solid m.p. 202–4° C.

¹H NMR (250 MHz, DMSO) δ: 3.28 (2H, t, J 8 Hz), 3.86 (3H, s), 4.18 (2H, t, J 8 Hz), 7.12 (1H, d, J 9 Hz), 7.22 ( 1H, s), 7.47 (1H, dd, J 7 Hz, 5 Hz), 7.51 (1H, m, J 7 Hz), 8.08 (1H, dd, J 8 Hz, 2 Hz), 8.10 (1H, s), 8.27 (1H, d, J 2 Hz), 8.40–8.47 (2H, m), 8.78 (1H, s).

MS (EI) m/e=431 (MH⁺)

EXAMPLE 54

5-Methoxy-6-trifluoromethyl-1-[4-(pyridin-4-ylmethyloxy)phenyl carbamoyl]indoline 4-(Pyridin-4-ylmethyloxy)aniline (0.5 g, 2.5 mmol) was converted to the phenyl carbamate and treated with 5-methoxy-6-trifluoromethylindoline (0.54 g, 2.5 mmol) as in the method of Example 52. Chromatography using ethyl acetate as eluant followed by recrystallisation from ethyl acetate/petroleum ether (60–80°) afforded the title compound (0.23 g, 24%) as an off-white crystalline solid m.p. 205–207° C.

¹H NMR (250 MHz, CDCl₃) δ: 3.26 (2H, t, J 8 Hz), 3.82 (3H, s), 4.07 (2H, t, J 8 Hz), 5.06 (2H, s), 6.29 (1H, s), 6.83 (1H, s), 6.91 (2H, d, J 10 Hz), 7.28–7.48 (4H, m), 8.22 (1H, s), 8.60 (2H, d, J 7 Hz).

MS (EI) m/e=444 (MH⁺)

EXAMPLE 55

5-Methoxy-6-trifluoromethyl-1-[6-(pyridin-4-ylmethyloxy)pyridin-3-ylcarbamoyl]indoline 5-Amino-2-(pyridin-4-ylmethyloxy)pyridine (0.5 g, 2.5 mmol) was converted to the phenyl carbamate and treated with 5-methoxy-6-trifluoromethylindoline (0.54 g, 2.5 mmol) as in the method of Example 52. Chromatography using ethyl acetate as eluant followed by recrystallisation from ethyl acetate/petroleum ether (60–80°) afforded the title compound (0.13 g, 13%) as an off-white solid m.p. 187–189° C.

¹H NMR (250 MHz, CDCl₃) δ: 3.31 (2H, t, J 8 Hz), 3.88 (3H, s), 4.12 (3H, t, J 8 Hz), 5.40 (2H, s), 6.32 (1H, s), 6.88 (1H, m), 7.35 (2H, d, J 6 Hz), 7.91 (1H, dd, J 8 Hz, 2 Hz), 8.04 (1H, d, J 2 Hz), 8.22 (1H, s), 8.59 (2H, d, J 6 Hz)

MS (EI) m/e=445 (MH⁺)

EXAMPLE 56

5-Methylthio-6-trifluoromethyl-1-[4-(pyrid-4-yl-methylamino carbonyl)phenyl carbamoyl]indoline This was prepared by the same methodology as for Example 69 affording the title compound in 11% yield as a white solid. m.p. 230–2° C.

¹H NMR (D6-DMSO) 2.50 (3H, s), 3.25 (2H, t), 3.45 (3H, s), 4.20 (2H, t), 7.15 (2H, d), 7.25 (2H, d), 7.50 (3H, m), 8.20 (1H, s), 8.45 (2H, d), 8.80 (1H, s)

EXAMPLE 57

Trans-5-Methylthio-6-trifluoromethyl-1-{4-[2-ethenyl-(4-pyridyl)]-phenyl carbamoyl}-indoline This was prepared from trans-4-[2-ethenyl-(4-pyridyl)]-aniline (D43) and 5-methylthio-6-trifluoromethyl indoline (D7) using the phenyl chloroformate procedure as for Description 18 and Example 26 affording the title compound as a yellow solid in 18% yield, m.p. 157–9° C.

¹H NMR (D6-DMSO) 2.50 (3H, s), 3.30 (2H, t), 4.25 (2H, t), 7.15 (1H, d), 7.45 (1H, s), 7.55 (2H, d), 7.65 (5H, m), 8.25 (1H, s), 8.55 (2H, d), 8.80 (1H, s)

EXAMPLE 58

5-Methylthio-6-trifluoromethyl-1-{4-[2-ethyl(4-pyridyl)]phenyl carbamoyl}indoline This was prepared by hydrogenation of D42 followed by coupling with 5-methylthio-6-trifluoromethyl indoline (D7) using the phenyl chloroformate method, affording the title compound in 20% yield as a white solid, m.p. 158–161° C.

¹H NMR (DMSO) 2.50 (3H, s), 2.85 (4H, m), 3.25 (2H, t), 4.20 (2H, t), 7.15 (2H, d), 7.25 (2H, d), 7.45 (4H, m), 8.20 (1H, s), 8.45 (2H, d), 8.60 (1H, s).

EXAMPLE 59

1-(1-(4-Pyridyl)-5-indolylcarbamoyl)-5-methoxy-6-trifluoromethylindoline

The title compound was prepared by the method of Example 73, from aminoindole (D53). Yield 62%, m.p. 206–211° C.

¹H NMR (CDCl₃) δ: 3.29 (2H, t, J=8), 3.85 (3H, s), 4.20 (2H, t, J=8), 6.78 (1H, d, J=3), 7.20 (1H, s), 7.41 (1H, dd, J=8,2), 7.72 (2H, d, J=6), 7.78 (1H, d, J=8), 7.83 (1H, d, J=3), 7.92 (1H, d, J=2), 8.16 (1H, s), 8.58 (1H, s), 8.70 (2H, d, J=6)

MS(API) m/z=453(MH⁺)

EXAMPLE 60

5-Methoxy-6-trifluoromethyl-1-[4-(pyridin-4-ylthiomethyl)phenyl carbamoyl]indoline 4-(Pyridin-4-ylthiomethyl)aniline (0.37 g, 1.71 mmol) was converted to the phenylcarbamate and treated with 5-methoxy-6-trifluoromethylindoline (D111) (0.37 g, 1.71 mmol) as in the method of Example 26 to give the title compound (0.5 g, 64%) as a white crystalline solid m.p. 174–5° C.

¹H NMR (250 MHz; DMSO) δ: 3.26 (2H, t, J 8 Hz), 3.84 (3H, s), 4.16 (2H, t, J 8 Hz), 4.32 (2H, s), 7.20 (1H, s), 7.32 (2H, d, J 7 Hz), 7.37 (2H, d, J 8 Hz), 7.52 (2H, d, J 8 Hz), 8.11 (1H, s), 8.37 (2H, d, J 7 Hz), 8.58 (1H, s).

MS(EI) m/e=460 (MH⁺)

EXAMPLE 61

5-Methoxy-6-trifluoromethyl-1-[4-(pyridin-4-ylsulphonylmethyl) phenylcarbamoyl]indoline 4-(Pyridin-4-ylsulphonylmethyl)aniline was converted to the title compound according the method of Example 60 to give a white crystalline solid (46%) m.p. 240–242° C.

¹H NMR (250 MHz; DMSO) δ: 3.26 (2H, t, J 8 Hz), 3.84 (3H, s), 4.17 (2H, t, J 8 Hz), 4.77 (2H, s), 7.08 (2H, d, J 8 Hz), 7.20 (1H, s), 7.50 (2H, d, J 8 Hz), 7.70 (2H, d, J 7 Hz), 8.10 (1H, s), 8.59 (1H, s), 8.88 (2H, d, J 7 Hz)

MS (EI) m/e=492 (MH⁺)

EXAMPLE 62

5-Methoxy-6-trifluoromethyl-1-[4-(pyridin-4-ylmethylthio)phenyl carbamoyl]indoline 4-(Pyridin-4-ylmethylthio)aniline was converted to the title compound according to the method of Example 60 to give a white crystalline solid (63%) m.p. 160–3° C.

¹H NMR (250 MHz; CDCl₃) δ: 3.27 (2H, t, J 8 Hz), 3.85 (3H, s), 3.95 (2H, s), 4.08 (2H, t, J 8 Hz), 6.41 (1H, s), 6.84 (1H, s), 7.12 (2H, d, J 7 Hz), 7.23 (2H, d, J 8 Hz), 7.33 (2H, d, J8 Hz), 8.21 (1H, s), 8.48 (2H, d, J 7 Hz).

MS (EI) m/e=460 (MH⁺)

EXAMPLE 63

5-Methylthio-6-trifluoromethyl-1-[(6-phenoxy)-3-pyridylcarbamoyl]-indoline

This was prepared from 6-phenoxy-3-aminopyridine and 5-methylthio-6-trifluoromethylindoline (D7) by similar methodology to Example 1, affording the title compound as a yellow solid in 39% yield, m.p. 86–88° C.

NMR (D6-DMSO) 2.50 (3H, s), 3.30 (2H, t), 4.20 (2H, t), 7.00 (1H, d), 7.10 (2H, m), 7.20 (1H, m), 7.45 (3H, m), 8.05 (1H, d), 8.20 (1H, s), 8.30 (1H, d), 8.85 (1H, s).

EXAMPLE 64

5-Methoxy-6-trifluoromethyl-1-[2-(pyridin-3-yloxy)pyridin-4-ylcarbamoyl)]indoline 4-Amino-2-(pyridin-3-yloxy)pyridine (D45) was converted to the title compound by the method of Example 60 to give an off-white crystalline solid (89%) m.p. 223–5° C.

¹H NMR (250 MHz; DMSO) δ: 3.28 (2H, t, J 8 Hz), 3.86 (3H, s), 4.21 (2H, t, J 8 Hz), 7.24 (1H, s), 7.39 (1H, s), 7.40–7.52 (2H, m), 7.62 (1H, m, J 9 Hz), 7.97 (1H, d, J 7 Hz), 8.13 (1H, s), 8.40–8.48 (2H, m), 9.10 (1H, s).

MS (EI) m/e=431 (MH⁺)

EXAMPLE 65

5-Methylthio-6-trifluoromethyl-1-[6-(2-methylpyridin-3-yloxy) pyridin-3-ylcarbamoyl]indoline 5-Amino-2-(2-methylpyridin-3-yloxy)pyridine was converted to the title compound according to the method of Example 60 to give a pale yellow solid (30%) m.p. 204–7° C.

¹H NMR (250 MHz; DMSO) δ: 3.28 (2H, t, J 8 Hz), 3.34 (3H, s), 4.19 (2H, t, J 8 Hz), 7.10 (1H, d, 8 Hz), 7.31 (1H, dd, J 8 Hz, 5 Hz), 7.44–7.53 (2H, m), 8.06 (1H, dd, J 8 Hz, 2 Hz), 8.21 (1H, s), 8.32 (2H, d, J 5 Hz), 8.82 (1H, s).

MS (EI) m/e=461 (MH⁺)

EXAMPLE 66

5-Methylthio-6-trifluoromethyl-1-[6-(6-methylpyridin-3-yloxy)pyridin-3-ylcarbamoyl]indoline 5-Amino-2-(6-methylpyridin-3-yloxy)pyridine was converted to the title compound according to the method of Example 60 to give an off-white solid (44%) m.p. 206–8° C.

¹H NMR (250 MHz; DMSO) δ: 3.28 (2H, t, J 8 Hz), 3.37 (3H, s), 4.19 (2H, t, J 8 Hz), 7.09 (1H, d, J 7 Hz), 7.32 (1H, d, J 7 Hz), 7.45–7.53 (2H, m), 8.06 (1H, dd, J 7 Hz, 2 Hz), 8.20 (1H, s), 8.24 (1H, d, J 2 Hz), 8.30 (1H, d, J 2 Hz), 8.84 (1H, s).

MS (EI) m/e=461 (MH⁺)

EXAMPLE 67

5-Methoxy-6-trifluoromethyl-1-[6-(pyridin-3-ylthio)pyridin-3-ylcarbamoyl]indoline 5-Amino-2-(pyridin-3-ylthio)pyridine was converted to the title compound according to the method of Example 60 to give a white crystalline solid (51%) m.p. 208–210° C.

¹H NMR (250 MHz; DMSO) δ: 3.28 (2H, t, J 8 Hz), 3.85 (3H, s), 4.17 (2H, t, J 8 Hz), 7.20 (1H, d, J 7 Hz), 7.22 (1H, s), 7.49 (1H, dd, J 7 Hz, 5 Hz), 7.90–7.99 (2H, m), 8.11 (1H, s), 8.57–8.68 (3H, m), 8.84 (1H, s).

MS(EI) m/e=447 (MH⁺)

EXAMPLE 68

5-Methylthio-6-trifluoromethyl-1-[4-(pyrid-3-ylmethyl)amido phenyl carbamoyl]indoline This was prepared in 61% yield by the same method as for Example 69, m.p. >250° C.

¹H NMR (D6-DMSO) δ: 2.50 (3H, s), 3.30 (2H, t), 4.25 (2H, t), 4.50 (2H, d), 7.40 (1H, m), 7.50 (1H, s), 7.70 (3H, m), 7.85 (2H, d), 8.25 (1H, s), 8.45 (1H, m), 8.55 (1H, m), 8.80 (1H, s), 9.00 (1H, t)

EXAMPLE 69
5-Methylthio-6-trifluoromethyl-1-[3-(pyrid-4-ylmethyl) amidophenylcarbamoyl]indoline A suspension of 5-methylthio-6-trifluoromethyl-1-(3-carboxyphenyl carbamoyl) indoline (D55) (0.5 g, 1.26 mmol) in dichloromethane (10 ml) was treated with oxalyl chloride (0.2 ml, 0.3 g, 2.4 mmol) and N,N-dimethyl formamide (3 drops). After 1 h the reaction mixture was evaporated to dryness. The residue was dissolved in tetrahydrofuran (20 ml) and added to a solution of 4-aminomethyl pyridine (0.15 ml, 1.39 mmol) and triethylamine (0.2 ml, 0.15 g, 1.5 mmol) in tetrahydrofuran (10 ml) at 0° C. After 1 h 5M aqueous sodium hydroxide solution (5 ml) was added, followed by water (20 ml). Filtration and drying afforded the product as a yellow solid (0.58 g, 94%) m.p. 122–3° C.

$^1$H NMR (D6-DMSO) δ: 2.50 (3H, s), 3.30 (2H, t), 4.20 (2H, t), 4.50 (2H, d), 7.30 (2H, d), 7.40 (1H, t), 7.45 (1H, s), 7.60 (1H, d), 7.80 (1H, d), 8.05 (1H, s), 8.25 (1H, s), 8.50 (2H, d), 8.85 (1H, bs), 9.15 (1H, t)

EXAMPLE 70
5-Methylthio-6-trifluoromethyl-1-[4-(pyrid-2-ylmethyl) amidophenylcarbamoyl]indoline This was prepared by the same method as for Example 69, affording the title compound as a white solid in 84% yield, m.p. 203–5° C.

$^1$H NMR (D6-DMSO) δ: 2.50 (3H, s), 3.30 (2H, t), 4.20 (2H, t), 4.55 (2H, d), 7.25–7.35 (2H, m), 7.45 (1H, s), 7.65–7.75 (3H, m), 7.90 (2H, d), 8.25 (1H, s), 8.50 (1H, d), 8.85 (1H, s), 9.00 (1H, t).

EXAMPLE 71
1-(1-(3-Pyridylmethyl)-5-indolylcarbamoyl)-5-methoxy-6-trifluoromethylindoline A solution of aminoinde (D48, 0.40 g, 1.8 mmol) and 1,1'-carbonyldiimidazole (0.30 g, 1.8 mmol) in dichloromethane (40 mL) was stirred at room temperature for 1.75 h, then evaporated. To the residue was added dimethylformamide (DMF, 10 mL) and a solution of 5-methoxy-6-trifluoromethylindoline (D111, 0.39 g, 1.8 mmol) in DMF (5mL). The mixture was stirred at 110° C. overnight, then poured into water and extracted with dichloromethane. The extract was washed with water, dried and evaporated. The residue was triturated with ether to give a grey solid, which was recrystallised from dichloromethane/methanol to give the title compound (0.15 g, 18%) m.p. 243–6° C.

$^1$H NMR (CDCl$_3$) δ: 3.26 (2H, t, J=8), 3.83 (3H, s), 4.17 (2H, t, J=8), 5.45 (2H, s), 6.45 (1H, d, J=3), 7.19 (1H, s), 7.22 (1H, d, J=8), 7.33 (1H, dd, J=7,5), 7.42 (1H, d, J=8), 7.51 (1H, d, J=3), 7.5 (1H, d, J=8), 7.72 (1H, s), 8.12 (1H, s), 8.41 (1H, s), 8.46 (1H, d, J=5), 8.51 (1H, s)

MS(API) m/z=467 (MH$^+$)

EXAMPLE 72
1-(1-(4-Pyridylmethyl)-5-indolylcarbamoyl)-5-methoxy-6-trifluoromethylindoline A mixture of aminoindole (D49, 0.46 g, 2.1 mmol), phenyl chloroformate (0.26 mL, 2.1 mmol) and triethylamine (0.29 mL, 2.1 mmol) in dichloromethane (5 mL) was stirred at room temperature for 1 h. The mixture was then diluted with dichloromethane, washed with water, dried and evaporated. The residue was dissolved in acetonitrile (10 mL). 5-Methoxy-6-trifluoromethylindoline (D11, 0.45 g, 2.1 mmol) and triethylamine (0.29 mL, 2.1 mmol) were added and the mixture was stirred for 3 h at room temperature. The reaction was worked up as for Example 71, and the solid obtained after trituration was recrystallised from dichloromethane/petrol to give the title compound (0.26 g, 27%), m.p. 215–8° C.

$^1$H NMR (CDCl$_3$) δ: 3.26 (2H, t, J=8), 3.83 (3H, s), 4.16 (2H, t, J=8), 5.48 (2H, s), 6.49 (1H, d, J=3), 7.04 (2H, d, J=6), 7.20 (2H, m), 7.30 (1H, d, J=8), 7.49 (1H, d, J=3), 7.73 (1H, s), 8.12 (1H, s), 8.42 (1H, s), 8.47 (2H, d, J=6).

MS(API) m/z=467(MH$^+$)

EXAMPLE 73
1-(1-(3-pyridyl)-5-indolylcarbamoyl)-5-methoxy-6-trifluoromethyl indoline The title compound was prepared by the method of Example 72, from aminoindoline (D52, 0.34 g, 1.63 mmol). Addition of the reaction mixture to water gave a precipitate which was filtered off, dried and recrystallised from dichloromethane/petrol to give the title compound (0.61 g, 84%), m.p. 202–4° C.

$^1$H NMR (CDCl$_3$) δ: 3.28 (2H, t, J=8), 3.84 (3H, s), 4.19 (2H, t, J=8), 6.73 (1H, d, J=3), 7.21 (1H, s), 7.38 (1H, dd, J=8,2), 7.55 (1H, d, J=8), 7.62 (1H, dd, J=7,5), 7.73 (1H, d, J=3), 7.89 (1H, d, J=2), 8.09 (1H, d, J=7), 8.17 (1H, s), 8.55 (1H, s), 8.60 (1H, d, J=5), 8.89 (1H, d, J=2).

MS(API) m/z=453(MH$^+$)

EXAMPLE 74
5-Methylthio-6-trifluoromethyl-1-{3-[2-(3-pyridyl)thiazol-4-yl]phenylcarbamoyl} indoline A solution of 4-(3-aminophenyl)-2-(3-pyridyl)-thiazole (0.76 g, 3 mmol) in chloroform (30 ml) was added to a solution of carbonyl diimidazole (0.49 g, 3 mmol) in dichloromethane (10 ml). After 1 h the mixture was evaporated. 5-Methylthio-6-trifluoromethyl indoline (0.7 g, 3 mmol) and N,N-dimethylformamide (20 ml) were added. The mixture was heated at 100° C. for 1 h, then diluted with water (50 ml). Filtration and evaporated afforded a yellow solid (1.1 g). Recrystallisation from ethyl acetate-petrol afforded the title compound as a white solid (0.53 g, 35%), m.p. 154–5° C.

$^1$H NMR (DMSO) 2.50 (3H, s), 3.30 (2H, t), 4.25 (2H, t), 7.45 (1H, t), 7.50 (1H, s), 7.55 (2H, m), 7.70 (1H, m), 8.25 (2H, m), 8.40 (1H, dt), 8.70 (1H, d), 8.80 (1H, s), 9.25 (1H, d).

EXAMPLE 75
5-Methylthio-6-trifluoromethyl-1-{4-[2-(4-pyridyl)-thiazol-4-yl]phenyl carbamoyl}indoline This was prepared in the same manner as 5-methylthio-6-trifluoromethyl-1-{3-[2-(3-pyridyl)-thiazol-4-yl]phenyl carbamoyl} indoline to give the product as a yellow solid (0.2 g, 31%), m.p. 253–4° C.

$^1$H NMR (DMSO) δ: 8.8 (3H, m), 8.2 (2H, s), 8.0 (4H, m), 7.7 (2H, d), 7.4 (1H, s), 4.2 (2H, t), 3.3 (2H, t), 2.5 (3H, s)

EXAMPLE 76
5-Methylthio-6-trifluoromethyl-1-{4-[2-(3-pyridyl)-thiazol-4-yl]phenylcarbamoyl}indoline This was prepared in the same manner as 5-methylthio-6-trifluoromethyl-1-{3-[2-(3-pyridyl)-thiazol-4-yl]phenyl carbamoyl} indoline to give the product as a yellow solid (0.25 g, 39%), m.p. >25° C.

$^1$H NMR (DMSO) δ: 9.2 (1H, s), 8.8 (1H, s), 8.7 (1H, d), 8.4 (1H, d), 8.2 (1H, s), 8.1 (1H, s), 7.95 (2H, d), 7.7 (2H, d), 7.6 (1H, q), 7.4 (1H, s), 4.2 (2H, t), 3.3 (2H, t), 2.5 (3H, s)

EXAMPLE 77
1-[4-Fluoro-3-(3-pyridyl)phenylcarbamoyl]-5-methoxy-6-trifluoromethyl indoline A solution of 4-fluoro-3-(pyrid-3-yl)phenylcarbonyl azide (D59) (270 mg, 1.1 mmol) in toluene (10 ml) was refluxed under argon for 45 minutes and cooled. To a stirred solution of the indoline (D11) (266 mg, 1.1 eq) in dichloromethane was added the isocyanate solution. The total solution was stirred at room temperature overnight, evaporated to dryness and chromatographed (EtOAc→5% MeOH/EtOAc, SiO$_2$). Concentration of fractions afforded the title compound as a white powder (315 mg, 66%). Melting point=210°–212° C.

$^1$H NMR (250 MHz, δ: 8.73 (d, 2H), 8.60 (dd, 1H), 8.10 (s, 1H), 7.97 (dd, 1H), 7.75 (m, 1H), 7.65 (m, 1H), 7.54 (m, 1H), 7.30 (t, 1H), 7.21 (s, 1H), 4.15 (t, 2H), 3.83 (s, 3H), 3.27 (t, 2H).

Mass spec: m/z=432 MH$^+$

EXAMPLE 78
1-[3-Fluoro-5-(pyrimidin-5-yl)phenylcarbamoyl]-5-methoxy-6-trifluoromethyl indoline 3-Fluoro-5-(pyrimidin-5-yl)phenylcarbonyl azide (D60) (0.22 g, 0.00091 mole) was dissolved in dry toluene (15 ml) and heated under reflux under argon for ½ hour. After cooling to ambient temperature, 5-methoxy-6-trifluoromethyl indoline (D11) (0.20 g, 0.00091 mole) in dichloromethane (8 ml) was added and the mixture stirred for 18 h. The dichloromethane was removed in vacuo and the resulting precipitate filtered and dried in vacuo. This was recrystallised from ethyl acetate/60–80° petroleum ether to afford the title compound (0.17 g, 43%).

$^1$H NMR (200 MHz, D$^6$DMSO) δ (ppm): 3.30 (2H, t, J=8), 3.87 (3H, s), 4.20 (2H, t, J=8), 7.22 (1H, s), 7.38 (1H, dt, J=3, 9), 7.68 (1H, dt, J=3, 11), 7.79 (1H, s), 8.14 (1H, s), 8.90 (1H, s), 9.12 (2H, s), 9.24 (1H, s).

EXAMPLE 79
1-[4-Chloro-3-(4-methyl-3-pyridyl)phenylcarbamoyl]-5-methoxy-6-trifluoromethylindoline 4-Chloro-3-(4-methyl-3-pyridyl)aniline (D62) was converted to the phenyl carbamate in the usual manner and then treated with 5-methoxy-6-trifluoromethylindoline (D11). Purification of the residue obtained by flash chromatography on silica gel gave the title compound (E79) (0.115 g, 49%) m.p. 140–141° C.

$^1$H NMR (CDCl$_3$) δ: 2.19 (3H, s), 3.28 (2H, t, J=8 Hz), 3.82 (3H, s), 4.15 (2H, t, J=8 Hz), 6.81 (1H, s), 7.09 (1H, s), 7.20 (1H, d, J=6 Hz), 7.25 (1H, s), 7.40 (1H, d, J=8 Hz), 7.52–7.59 (1H, m), 8.20 (1H, s), 8.30 (1H, s), 8.45 (1H, d, J=6 Hz).

EXAMPLE 80
1-[2,3-Dihydro-7-(pyrid-3-yl)benzofuran-5-ylcarbamoyl]-5-methoxy-6-trifluoromethyl indoline Phenyl N-[2,3-dihydro-7-(pyrid-3-yl)benzofuran-5-yl] carbamate (D65) (0.20 g, 0.00060mole) in dry DMF (10 ml) was treated under argon with 5-methoxy-6 trifluoromethyl indoline (D11) (0.13 g, 0.00060 mole) and heated under reflux for 18 hours. The reaction was allowed to cool to ambient temperature and the solvent was removed in vacuo. The residue was dissolved in dichloromethane, washed with deionised water and 10% sodium hydroxide solution, dried (Na$_2$SO$_4$) and evaporated in vacuo. The resulting brown oil was purified by flash column chromatography on silica gel, eluting with 2% methanol/dichloromethane, followed by recrystallisation from ethyl acetate 60–80° petroleum ether to afford the title compound (0.07 g, 26%) as a beige solid.

$^1$H NMR (200 MHz, D$^6$DMSO) δ (ppm): 3.12–3.49 (4H, m), 3.85 (3H, s), 4.15 (2H, t, J=8), 4.61 (2H, t, J=10), 7.21 (1H, s), 7.40–7.58 (3H, m), 8.07 (1H, dt, J=1, 7), 8.13 (1H, s), 8.43–8.60 (2H, m), 8.88 (1H, d, J=1).

EXAMPLE 81
5-Methoxy-6-trifluoromethyl-1-[6-(2-methylpyridin-3-yloxy)pyridin-3-ylcarbamoyl]indoline 5-Amino-2-(2-methylpyridin-3-yloxy)pyridine was converted to the title compound according to the method of Example 60 to give a white crystalline solid (71%) m.p. 227–230° C.

$^1$H NMR (250 MHz, DMSO) δ: 3.28 (2H, t, J8 Hz), 3.85 (3H, s), 4.15 (2H, t, J8 Hz), 7.09 (1H, d, J8 Hz), 7.21 (1H, s), 7.30 (1H, dd, J8 Hz, 5 Hz), 7.49 (1H, d, J8 Hz), 8.04 (1H, dd, J8 Hz, 2 Hz), 8.10 (1H, d, J2 Hz), 8.32 (1H, d, J5 Hz), 8.72 (1H, s).

MS(EI) m/e=445 (MH$^+$)

EXAMPLE 82
5-Methoxy-6-trifluoromethyl-1-[6-(4-methylpyridin-3-yloxy)pyridin-3-ylcarbamoyl]indoline 5-Amino-2-(4-methylpyridin-3-yloxy)pyridine was converted to the title compound according to the method of Example 60 to give a white crystalline solid (51%) m.p. 188–191° C.

$^1$H NMR (250 MHz, DMSO) δ: 3.30 (2H, t, J8 Hz), 3.83 (3H, s), 4.15 (2H, t, J8 Hz), 7.10 (1H, d, J8 Hz), 7.20 (1H, s), 7.38 (1H, d, J5 Hz), 8.04 (1H, dd, J8 Hz, 2 Hz), 8.10 (1H, s), 8.17 (1H, d, J2 Hz), 8.29 (1H, s), 8.30 (1H, d, J5 Hz), 8.72 (1H, s).

MS (EI) m/e=445 (MH$^+$)

The following examples were prepared using similar techniques:

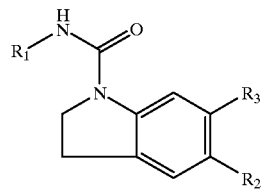

| Example No. | R$_1$ | R$_2$ | R$_3$ | M.Pt. ° C. |
|---|---|---|---|---|
| 83 | 3-(3-Pyridyl)phenyl | OMe | CF$_3$ | 192–193 |
| 84 | 2-Methoxy-3-(3-pyridyl)phenyl | OMe | CF$_3$ | 196–197 |
| 85 | 2-Chloro-3-(3-pyridyl)phenyl | OMe | CF$_3$ | 214–216 |

-continued

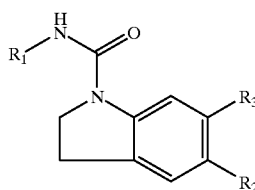

| Example No. | R₁ | R₂ | R₃ | M.Pt. °C. |
|---|---|---|---|---|
| 86 | 3-(3-Quinolyl)phenyl | OMe | $CF_3$ | 240 (dec.) |
| 87 | 5-(4-Fluorophenyl)-3-pyridyl | OMe | $CF_3$ | >200 |
| 88 | 5-(3,5-Difluorophenyl)-3-pyridyl | OMe | $CF_3$ | 226–229 |
| 89 | 5-(4-Chlorophenyl)-3-pyridyl | OMe | $CF_3$ | 198–199 |
| 90 | 5-(2-Methylphenyl)-3-pyridyl | OMe | $CF_3$ | 103–105 |
| 91 | 5-(2-Formylphenyl)-3-pyridyl | OMe | $CF_3$ | 114–116 |
| 92 | 5-(2-Hydroxymethylphenyl)-3-pyridyl | OMe | $CF_3$ | 190–192 |
| 93 | 5-(3-Chloro-4-fluorophenyl)-3-pyridyl | OMe | $CF_3$ | 113–115 |
| 94 | 6-Phenyl-3-pyridyl | OMe | $CF_3$ | 204–207 |
| 95 | 5-(3-pyridyl)-2-pyridyl | OMe | $CF_3$ | >225 |
| 96 | 6-(1-Pyrazolyl)-3-pyridyl | OMe | $CF_3$ | >225 |
| 97 | 3-(4-N,N-Dimethylaminophenyl)phenyl | OMe | $CF_3$ | 213–215 |
| 98 | 3-(4-N,N-Dimethylaminomethylphenyl)phenyl | OMe | $CF_3$ | 209–211 |
| 99 | 3-(3-N,N-Dimethylaminomethylphenyl)phenyl | OMe | $CF_3$ | 185–187 |
| 100 | 3-(5-N,N-Dimethylaminomethyl-1,2,4-oxadiazol-3-yl)phenyl | OMe | $CF_3$ | 154–155 |
| 101 | 3-(1-Dimethylaminoethyl-2-pyrrolyl)phenyl | OMe | $CF_3$ | 158–159 |
| 102 | 3-(2-Pyrrolyl)phenyl | OMe | $CF_3$ | >240 |
| 103 | 3-(3-Pyridyl)phenyl | Me | Cl | 208–210 |
| 104 | 5-Ethenyl-3-(3-pyridyl)phenyl | OMe | $CF_3$ | 138–140 |
| 105 | 3-(3-Pyridyl)-5-(trifluoromethyl)phenyl | OMe | $CF_3$ | 220–222 |
| 106 | 5-Chloro-3-(3-pyridyl)phenyl | OMe | $CF_3$ | 183–185 |
| 107 | 5-Acetyl-3-(3-pyridyl)phenyl | OMe | $CF_3$ | 174–176 |
| 108 | 4-Methoxy-3-(3-pyridyl)-5-(trifluoromethyl)phenyl | OMe | $CF_3$ | 180–181 |
| 109 | 4-Methyl-3-(4-methyl-3-pyridyl)phenyl | OMe | $CF_3$ | 153–155 |
| 110 | 3-(2-Methyl-3-pyridyl)phenyl | OMe | $CF_3$ | 179–180 |
| 111 | 3-(2,4-Dimethyl-3-pyridyl)phenyl | OMe | $CF_3$ | 202–204 |
| 112 | 3-(6-Methyl-3-pyridyl)phenyl | OMe | $CF_3$ | 228–230 |
| 113 | 3-(2-Methyl-4-pyrimidinyl)phenyl | OMe | $CF_3$ | >220 |
| 114 | 3,5-(Di-3-pyridyl)phenyl | OMe | $CF_3$ | 155–156 |
| 115 | 3-(3-Pyridyl)-5-(4-pyridyl)phenyl | OMe | $CF_3$ | 153–154 |
| 116 | 5-Fluoro-3-(6-methyl-3-pyridyl)phenyl | OMe | $CF_3$ | 213–215 |
| 117 | 3-(4,6-Dimethyl-3-pyridyl)phenyl | OMe | $CF_3$ | 161–162 |
| 118 | 5-Fluoro-3-(3-pyridazinyl)phenyl | OMe | $CF_3$ | 230–231 |
| 119 | 3-(5-Pyrimidinyl)phenyl | OMe | $CF_3$ | 245–250 |
| 120 | 3-(2-Pyrazinyl)phenyl | OMe | $CF_3$ | 208–209 |
| 121 | 3-(6-Methyl-3-pyridazinyl)phenyl | OMe | $CF_3$ | 229–231 |
| 122 | 3-(3-Pyridyl)-5-(trifluoromethoxy)phenyl | OMe | $CF_3$ | 168–170 |
| 123 | 3-(3-Pyridyl)-4-(trifluoromethoxy)phenyl | OMe | $CF_3$ | 99–100 |
| 124 | 5-Fluoro-4-methyl-3-(3-pyridyl)phenyl | OMe | $CF_3$ | 244–247 |
| 125 | 5-Fluoro-3-(2-methyl-3-pyridyl)phenyl | OMe | $CF_3$ | 204–205 |
| 126 | 5-Fluoro-3-(2-pyrazinyl)phenyl | OMe | $CF_3$ | 230–231 |
| 127 | 5-Fluoro-3-(4,6-dimethylpyrid-3-yl)phenyl | OMe | $CF_3$ | 215–218 |
| 128 | 5-Fluoro-4-methyl-3-(pyrimidin-3-yl)phenyl | OMe | $CF_3$ | 188–189 |
| 129 | 5-Fluoro-4-methyl-3-(pyrid-3-yl)phenyl | Me | Cl | 233–235 |
| 130 | 5-(5-Pyrimidinyl)-3-pyridyl | OMe | $CF_3$ | 120–121, 215–216 |
| 131 | 5-Fluoro-3-(2-pyrazinyl)phenyl | Me | Cl | 226–227 |
| 132 | 5-Fluoro-3-(5-pyrimidinyl)phenyl | Me | Cl | 222–226 |
| 133 | 3-(3-Pyridyl)phenyl | $C(Me_2)CH_2CH_2$ | | 91–92 |
| 134 | 5-Fluoro-3-(2-methyl-3-pyridyl)phenyl | Me | Cl | 205–206 |
| 135 | 4-Fluoro-3-(3-pyridyl)phenyl | Cl | Cl | 200–202 |
| 136 | 4-Fluoro-3-(3-pyridyl)phenyl | Me | Cl | 185–186 |
| 137 | 3-(Pyrid-3-ylmethyloxy)phenyl | OMe | $CF_3$ | 202–204 |
| 138 | 4-(Pyrid-3-ylmethyloxy)phenyl | OMe | $CF_3$ | 215–217 |
| 139 | 3-(Pyrid-3-yloxymethyl)phenyl | OMe | $CF_3$ | 188–190 |
| 140 | 5-Methyl-6-(pyrid-3-yl)pyrid-3-yl | OMe | $CF_3$ | 230–232 |
| 141 | 5-Chloro-6-(pyrid-3-yl)pyrid-3-yl | SMe | $CF_3$ | 245–250 |
| 142 | 6-(5-Chloropyrid-3-yl)pyrid-3-yl | SMe | $CF_3$ | 193–195 |

-continued

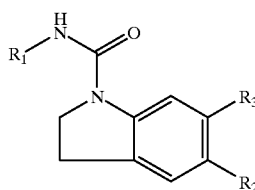

| Example No. | R₁ | R₂ | R₃ | M.Pt. °C. |
|---|---|---|---|---|
| 143 | 4-(Pyrid-3-yloxy)phenyl | OMe | $CF_3$ | 193–194 |
| 144 | 6-(Pyrid-3-ylthio)pyrid-3-yl | SMe | $CF_3$ | 204–206 |
| 145 | 6-(Pyrid-4-ylthio)pyrid-3-yl | SMe | $CF_3$ | 214–216 |
| 146 | 6-(Pyrid-4-ylthio)pyrid-3-yl | OMe | $CF_3$ | 204–206 |
| 147 | 4-(Pyrid-4-ylmethyl)phenyl | SMe | $CF_3$ | 206–209 |
| 148 | 3-(Pyrid-3-ylmethylaminocarbonyl)phenyl | SMe | $CF_3$ | 210–215 |
| 149 | 3-[3-(Pyrid-2-yl)propionyl]phenyl | SMe | $CF_3$ | 145–146 |
| 150 | 3-[3-(Pyrid-2-yl)-1-hydroxypropyl]phenyl | SMe | $CF_3$ | 78–80 |
| 151 | 4-(Pyrid-4-ylmethylaminocarbonyl)phenyl | SMe | $CF_3$ | 138–140 |
| 152 | 3-[1-(Pyrid-2-yl)propionyl]phenyl | SMe | $CF_3$ | 110–112 |
| 153 | 3-[2-(Pyrid-2-yl)ethylcarbamoyl]phenyl | SMe | $CF_3$ | 92–94 |
| 154 | 3-[(Pyrid-2-yl)methylcarbamoyl]phenyl | SMe | $CF_3$ | 116–118 |
| 155 | 6-(Phenoxy)pyrid-3-yl | OMe | $CF_3$ | 202–203 |
| 156 | 6-(2,4-Dimethylpyrid-3-yloxy)pyrid-3-yl | OMe | $CF_3$ | 218–221 |
| 157 | 6-(2-Methylphenoxy)pyrid-3-yl | OMe | $CF_3$ | 226–228 |
| 158 | 6-(3-Methoxyphenoxy)pyrid-3-yl | OMe | $CF_3$ | 188–189 |
| 159 | 6-(4-Fluoro-2-methylphenoxy)pyrid-3-yl | OMe | $CF_3$ | 208–209 |
| 160 | 6-(2,4-Dimethylphenoxy)pyrid-3-yl | OMe | $CF_3$ | 236–238 |
| 161 | 6-(2-Chloropyrid-3-yloxy)pyrid-3-yl | OMe | $CF_3$ | 238–240 |
| 162 | 6-(2-Ethylphenoxy)pyrid-3-yl | OMe | $CF_3$ | 215–220 |
| 163 | 6-(4-Carbamoylphenoxy)pyrid-3-yl | OMe | $CF_3$ | 245–248 |
| 164 | 6-(2-Trifluoromethylphenoxy)pyrid-3-yl | OMe | $CF_3$ | 237–238 |
| 165 | 6-(3-Trifluoromethylphenoxy)pyrid-3-yl | OMe | $CF_3$ | 193–194 |
| 166 | 6-(2,6-Dimethylpyrid-3-yloxy)pyrid-3-yl | OMe | $CF_3$ | 230–233 |
| 167 | 6-(2-Methylpyrid-3-yloxy)pyrid-3-yl | Me | Cl | 181–183 |
| 168 | 6-(2-Methylpyrid-3-yloxy)pyrid-3-yl | Cl | Cl | 225–228 |
| 169 | 4-Fluoro-3-(5-pyrimidinyl)phenyl | Cl | Cl | 132–135 |
| 170 | 5-Fluoro-3-(5-pyrimidinyl)phenyl | Cl | Cl | 260 |
| 171 | 4-Fluoro-3-(5-pyrimidinyl)phenyl | Me | Cl | 211–213 |
| 172 | 5-Fluoro-3-(5-pyrimidinyl)phenyl | Br | $CF_3$ | 214–218 |
| 173 | 6-(2-Methyl-1-oxopyrid-3-yloxy)pyrid-3-yl | OMe | $CF_3$ | 252–257 |
| 174 | 4-Fluoro-3-(3-pyridyl)phenyl | Br | $CF_3$ | 200–201 |
| 175 | 6-(3-Cyanophenoxy)pyrid-3-yl | OMe | $CF_3$ | 136–138 |
| 176 | 6-(4-Cyanophenoxy)pyrid-3-yl | OMe | $CF_3$ | 188–189 |
| 177 | 6-(2-Methylpyrid-3-yloxy)pyrid-3-yl | Br | $CF_3$ | 211–213 |

Pharmacological data

[$^3$H]-mesulergine binding to rat or human 5-HT$_{2C}$ clones expressed in 293 cells in vitro Compounds were tested following the procedure outlined in WO 94/04533. The compounds of examples 1 to 165 have pKi values of 5.8 to 9.7.

Reversal of MCPP-induced Hypolocomotion

Compounds were tested following the procedure outlined in WO 94/04533. The compound of examples 1, 3, 7, 8, 21, 24, 25, 26, 31, 40, 42, 52, 53, 54, 55, 77, 78, 79, 80 and 81 have ID$_{50's}$ between 0.5 and 5.5 mg/kg p.o.

We claim:

1. A compound of formula (I) or a salt thereof:

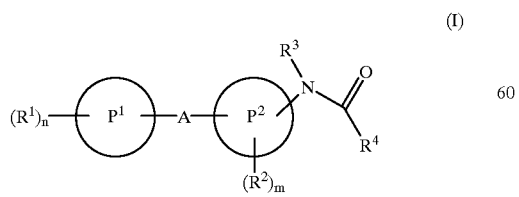

(I)

wherein:

P¹ is pyridyl;

P² is phenyl;

A is a bond or a chain of 1 to 5 atoms optionally substituted by $C_{1-6}$alkyl;

R¹ and R² groups are each independently hydrogen, $C_{1-6}$alkyl optionally substituted by NR$^{12}$R$^{13}$, $C_{2-6}$alkenyl, $C_{2-6}$alkynyl, cyano, halogen, $CF_3$, NR$^{12}$R$^{13}$, CHO, OCF$_3$, COR$^{14}$, CH$_2$OR$^{14}$ or OR$^{14}$ where R$^{12}$, R$^{13}$ and R$^{14}$ are independently hydrogen or $C_{1-6}$alkyl;

n and m are independently 0, 1 or 2;

R³ is hydrogen or $C_{1-6}$ alkyl;

R⁴ is a group of formula (i):

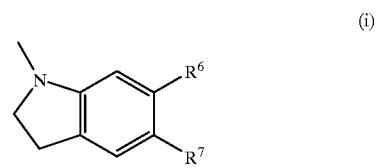

(i)

in which:

R⁶ and R⁷ are independently hydrogen, $C_{1-6}$alkyl optionally substituted by one or more fluorine atoms, $C_{1-6}$alkylthio, $C_{1-6}$alkoxy or halogen, or a pharmaceutically acceptable salt thereof.

2. A compound according to claim 1 which is:
1-[(3-Pyridyl)-3-phenyl carbamoyl]-5-methoxy-6-trifluoromethyl indoline,
1-[(4-Pyridyl)-3-phenyl carbamoyl]-5-methylthio-6-trifluoromethyl indoline,
1-[(3-Pyridyl)-3-phenyl carbamoyl]-5-methylthio-6-trifluoromethyl indoline,
1-[(3-Pyridyl)-4-phenyl carbamoyl]-5-methoxy-6-triflouromethylindoline,
1-[(4-Pyridyl)-4-phenyl carbamoyl]-5-methoxy-6-trifluoromethyl indoline,
1-[(2-Pyridyl)-3-phenyl carbamoyl]-5-methoxy-6-trifluoromethyl indoline,
1-[4-Methyl-3-(3-Pyridyl)-phenylcarbamoyl]-5-methoxy-6-trifluoromethyl indoline,
1-[2-Fluoro-5-(3-pyridyl) phenyl carbamoyl]-5-methoxy-6-trifluoromethyl indoline,
1-(3-Fluoro-5-(4-methyl-3-pyridyl)phenylcarbamoyl)-5-methoxy-6-trifluoromethylindoline,
6-Chloro-5-methyl-1-(4-methyl-3-(pyrid-3-yl)-phenylcarbamoyl) indoline,
1-(4-Methyl-3-(pyrid-3-yl) phenylcarbamoyl)-5-thiomethyl-6-trifluoromethyl indoline,
1-(3-Fluoro-5-(pyrid-3-yl)phenylcarbamoyl)-5-thiomethyl-6-trifluoromethyl-indoline,
1-(4-Chloro-3-(pyrid-3-yl)phenylcarbamoyl)-5-methoxy-6-trifluoromethylindoline,
1-[4-Methyl-3-(4-methyl-3-pyridyl)phenylcarbamoyl]-5-methoxy-6-trifluoromethyl indoline,
1-[5-Bromo-3-(pyrid-3-yl)phenylcarbamoyl]-5-methoxy-6-trifluoromethylindoline,
1-[4-t-Butyl-3-(pyrid-3-yl)phenylcarbamoyl]-5-methoxy-6-trifluoromethylindoline,
1-[4-Methoxy-3-(pyrid-3-yl)phenylcarbamoyl]-5-methoxy-6-trifluoromethylindoline,
1-[5-Fluoro-4-methoxy-3-(pyrid-3-yl)phenylcarbamoyl]-5-methoxy-6-trifluoromethylindoline,
1-[3-Bromo-4-methyl-5-(3-pyridyl)phenylcarbamoyl]-5-methoxy-6-trifluoromethylindoline,
1-[3-(4-Methyl-3-pyridyl)phenylcarbamoyl]-5-methoxy-6-trifluoromethylindoline,
1-[5-Ethyl-3-(pyrid-3-yl)phenylcarbamoyl]-5-methoxy-6-trifluoromethylindoline,
6-Chloro-5-methyl-1-[4-methyl-3-(4-methyl-3-pyridyl) phenyl carbamoyl] indoline,
1-[3-(pyrid-3-ylaminocarbonyl)-phenylcarbamoyl]-5-methoxy-6-trifluoromethyl-indoline,
1-[3-(Pyrid-3-ylaminocarbonyl )-phenylcarbamoyl]-5-methylthio-6-trifluoromethyl-indoline,
1-[3-(Pyrid-4-ylaminocarbonyl)-phenylcarbamoyl]-5-methylthio-6-trifluoromethyl indoline,
1-[4-(Pyrid-3-ylaminocarbonyl)-phenylcarbamoyl]-5-methylthio-6-trifluoromethyl indoline,
1-[4-(Pyrid-4-ylaminocarbonyl)-phenylcarbamoyl]-5-methylthio-6-trifluoromethyl indoline,
1-[3-(3-pyridylcarbonyl)phenylcarbamoyl]-5-methoxy-6-trifluoromethyl indoline,
1-[3-(Pyrid-3-yl-aminosulphonyl)-phenylcarbamoyl]5-methoxy-6-trifluoromethyl-indoline, 5-Methylthio-6-trifluoromethyl-1-[4-(pyrid-4-yl-methylamino carbonyl) phenyl carbamoyl] indoline,
Trans-5-Methylthio-6-trifluoromethyl-1-{4-[2-ethenyl-(4-pyridyl)]-phenyl carbamoyl}-indoline,
5-Methylthio-6-trifluoromethyl-1-{4-[2-ethyl(4-pyridyl)] phenyl carbamoyl}indoline,
5-Methylthio-6-trifluoromethyl-1-[4-(pyrid-3-ylmethyl) amido phenyl carbamoyl]indoline,
5-Methylthio-6-trifluoromethyl-1-[3-(pyrid-4-ylmethyl) amidophenylcarbamoyl] indoline,
5-Methylthio-6-trifluoromethyl-1-[4-(pyrid-2-ylmethyl) amidophenylcarbamoyl] indoline,
1-[4-Fluoro-3-(3-pyridyl)phenylcarbamoyl]-5-methoxy-6-trifluoromethyl indoline,
1-[4-Chloro-3-(4-methyl-3-pyridyl)phenylcarbamoyl]-5-methoxy-6-trifluoromethylindoline, and pharmaceutically acceptable salts thereof.

3. A compound according to claim 1 in which A is a bond.

4. A compound according to claim 1 in which $R^2$ is hydrogen, halogen, methyl, $CF_3$ or $OCF_3$.

5. A compound according to claim 1 in which $R^3$ is hydrogen.

6. A compound according to claim 1 in which $R^6$ is trifluoromethyl or halogen and $R^7$ is $C_{1-6}$ alkoxy, $C_{1-6}$alkylthio or $C_{1-6}$ alkyl.

7. A pharmaceutical composition which comprises a compound according to claim 1 and a pharmaceutically acceptable carrier or excipient.

8. A process for the preparation of a compound of formula (I) or a pharmaceutically acceptable salt thereof, which process comprises:

(a) the coupling of a compound of formula (II);

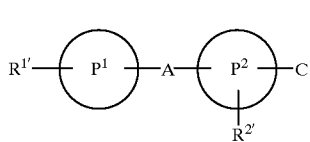

(II)

with a compound of formula (HI);

(III)

wherein A, $P^1$ and $P^2$ are as defined in formula (I) , C and D contain the appropriate functional group(s) necessary to form the moiety -NR$^{3'}$CO when coupled, the variables $R^{1'}$, $R^{2'}$, $R^{3'}$ and $R^{4'}$ are $R^1$, $R^2$, $R^3$ and $R^4$ respectively, as defined in formula (I), or groups convertible thereto, and thereafter optionally and as necessary and in any appropriate order, converting any $R^{1'}$, $R^{2'}$, $R^{3'}$ and $R^{4'}$, when other than $R^1$, $R^2$, $R^3$ and $R^4$ respectively to $R^1$, $R^2$, $R^3$ and $R^4$, interconverting $R^1$, $R^2$, $R^3$ and $R^4$ and forming a pharmaceutically acceptable salt thereof; or (b) the coupling of a compound of formula (IV);

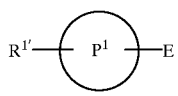

(IV)

with a compound of formula (V);

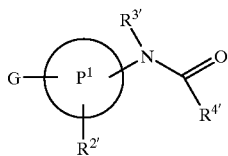

(V)

wherein $P^1$, $P^2$, $R^{1'}$, $R^{2'}$, $R^{3'}$ and $R^{4'}$ are as defined above and E and G contain the appropriate functional group(s) necessary to form the A moiety when coupled and thereafter optionally and as necessary and in any appropriate order, converting any $R^{1'}$, $R^{2'}$, $R^{3'}$ and $R^{4'}$, when other than $R^1$, $R^2$, $R^3$ and $R^4$ respectively to $R^1$, $R^2$, $R^3$ and $R^4$, interconverting $R^1$, $R^2$, $R^3$ and $R^4$ and forming a pharmaceutically acceptable salt.

9. A method of antagonizing $5HT_{2C}$ receptors by administering to patient in need thereof, a compound of claim 1.

10. A method of treating CNS disorders by administering to a patient in need thereof, a compound of claim 1.

11. A method of treating anxiety or depression by administering to a patient in need thereof, a compound of claim 1.

12. A compound of claim 1 which is 1-[3-Fluoro-5-(3-pyridyl)phenylcarbomoyl]-5-methoxy-6-trifluoromethyl indoline.

13. A method of treating anxiety or depression by administering to a patient in need thereof, a compound of claim 12.

14. A pharmaceutical composition which comprises a compound according to claim 12 and a pharmaceutically acceptable carrier or excipient.

\* \* \* \* \*